(12) United States Patent
Kern et al.

(10) Patent No.: US 12,403,077 B2
(45) Date of Patent: Sep. 2, 2025

(54) USE OF A NEW COMPOSITION FOR PREVENTING OR SLOWING THE APPEARANCE OF SIGNS OF INFLAMMATION

(71) Applicant: SOCIETE D'EXPLOITATION DE PRODUITS POUR LES INDUSTRIES CHIMIQUES SEPPIC, Paris (FR)

(72) Inventors: Catherine Kern, Paris (FR); Christine Garcia, Castres (FR); Christian Gombert, Paris (FR); Philippe Msika, Paris (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 880 days.

(21) Appl. No.: 17/046,538

(22) PCT Filed: Apr. 12, 2019

(86) PCT No.: PCT/FR2019/050870
§ 371 (c)(1),
(2) Date: Oct. 9, 2020

(87) PCT Pub. No.: WO2019/197789
PCT Pub. Date: Oct. 17, 2019

(65) Prior Publication Data
US 2021/0154112 A1 May 27, 2021

(30) Foreign Application Priority Data
Apr. 13, 2018 (FR) ..................... 1853265

(51) Int. Cl.
*A61K 8/37* (2006.01)
*A61Q 19/00* (2006.01)

(52) U.S. Cl.
CPC ............... *A61K 8/37* (2013.01); *A61Q 19/00* (2013.01); *A61K 2800/75* (2013.01)

(58) Field of Classification Search
CPC ...... A61K 8/37; A61K 2800/75; A61K 8/368; A61Q 19/00; A61Q 19/005; A61P 17/00
See application file for complete search history.

(56) References Cited

U.S. PATENT DOCUMENTS

| 4,363,815 A | 12/1982 | Yu et al. | |
|---|---|---|---|
| 2004/0170581 A1* | 9/2004 | Henry | A61Q 19/00 424/59 |
| 2007/0004647 A1 | 1/2007 | Arbiser | |
| 2017/0035666 A1* | 2/2017 | Albert | A61K 8/86 |
| 2017/0136077 A1 | 5/2017 | Hines et al. | |

FOREIGN PATENT DOCUMENTS

| CN | 106074663 | 11/2016 |
|---|---|---|
| EP | 0 971 683 | 1/2000 |
| EP | 0 977 626 | 10/2002 |
| EP | 1 515 688 | 3/2005 |
| FR | 2 762 317 | 10/1998 |
| FR | 3047177 A1 * | 8/2017 |
| JP | 2011-207799 | 10/2011 |
| WO | 94/26694 | 11/1994 |
| WO | 96/00719 | 1/1996 |
| WO | 98/09611 | 3/1998 |
| WO | 98/44902 | 10/1998 |
| WO | 03/103616 | 12/2003 |
| WO | 2005/040230 | 5/2005 |
| WO | 2006/127525 | 11/2006 |
| WO | 2012/098342 | 7/2012 |

OTHER PUBLICATIONS

Office Action issued in Chinese Patent Application No. 201980024367.8 dated Aug. 17, 2022.
Chan et al., "A review of the pharmacological effects of *Arctium lappa* (burdock)," Inflammopharmacol, 2011, vol. 19, pp. 245-254.
Pirvu et al., "Comparative Studies on Analytical, Antioxidant, and Antimicrobial Activities of a Series of Vegetal Extracts Prepared from Eight Plant Species Growing in Romania," Journal of Planar Chromatography, vol. 27, 2014, pp. 346-356.
Jiang et al., "Caffeoylquinic acid derivatives from the roots of *Arctium lappa* L. (burdock) and their structure-activity relationships (SARs) of free radical scavenging activities," Phytochemistry Letters, vol. 15, Jan. 8, 2016, pp. 159-163.

(Continued)

*Primary Examiner* — David Browe
(74) *Attorney, Agent, or Firm* — NIXON & VANDERHYE

(57) ABSTRACT

A composition that prevents or slows the appearance of blemishes associated with inflammation of the skin and/or scalp, includes per 100% by mass: a) 60.0%-75.0% by mass of an organic solvent chosen from 1,2-propanediol, 1,3-propanediol, 1,4-butanediol, 1,3-butanediol, 1,2-butanediol, 2-methyl-2,4-pentanediol, 1,6-hexanediol, 1,8-octanediol, or a blend of the above compounds; b) 0.1%-2.0% by mass of a composition including a mass quantity $x_1$, expressed as mass equivalent of 1-O-(2-caffeyol)maloyl-3,5-O-dicaffeoylquinic acid, greater than or equal to 200 mg/g of a compound of general formula (I):

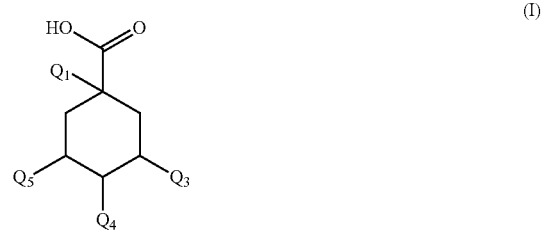

(I)

in which $Q_1$ and $Q_3$-$Q_5$ independently of each other represent the hydroxyl radical or a salt thereof or a radical selected among the caffeoyl, maloyl, caffeoyl maloyl and maloyl caffeoyl radicals; at least one of $Q_1$ and $Q_3$-$Q_5$ represents neither the —OH radical nor a salt thereof; and c) 20.0%-35.0% by mass water.

2 Claims, No Drawings

(56) References Cited

OTHER PUBLICATIONS

Zou et al., "Isolation and characterization of two new phenolic acids from cultured cells of Saussurea involucrata," Phytochemistry Letters, vol. 7, Feb. 1, 2014, pp. 133-136.
International Search Report for PCT/FR2019/050870 dated Sep. 30, 2019, 7 pages.
Written Opinion of the ISA for PCT/FR2019/050870 dated Sep. 30, 2019, 6 pages.
French Search Report for French Application No. 1853265 dated Nov. 20, 2018, 3 pages.

* cited by examiner

USE OF A NEW COMPOSITION FOR PREVENTING OR SLOWING THE APPEARANCE OF SIGNS OF INFLAMMATION

CROSS-REFERENCE TO RELATED APPLICATIONS

This application is the U.S. national phase of International Application No. PCT/FR2019/050870 filed Apr. 12, 2019 which designated the U.S. and claims priority to French Application No. 1853265 filed Apr. 13, 2018, the entire contents of each of which are hereby incorporated by reference.

BACKGROUND OF THE INVENTION

Field of the Invention

The subject of the present invention is the use of a composition comprising polysubstituted quinic acid derivatives, and more particularly of an extract of the plant *Arctium lappa* comprising said derivatives, for preparing formulations for topical use that are intended for preventing or slowing the appearance of the unesthetic signs associated with inflammation of the skin and/or of the scalp, and more particularly of reactive and/or sensitive skins.

Description of the Related Art

As human skin constitutes the first image seen by others, improving its appearance is often a subject of concern for human beings. The skin is the reflection either of a state of well-being, often associated with a clear or glowing skin, or else, conversely, of a state of tiredness, often associated with the unesthetic effects of irritated skin, such as, for example, the presence of redness on the skin and, more particularly, on certain parts of the face such as the cheeks, neck, and forehead. This redness comes about more particularly in the wake of numerous external stresses (such as, for example, changes in temperature) and affects particularly skin which is sensitive and reactive.

The skin is an atypical organ of the human body, which is extremely thin with regard to its extent, but also an individual's heaviest organ. One of the characteristics of the skin lies in the fact that it is an interface organ, a boundary organ, between the internal medium (human body) and the external medium. As a result, and with the flora which covers it and lives thereon, the skin is the first barrier for protecting the human body.

On account of its interface position with the external medium, the skin is subjected to numerous daily stresses, for instance contact with clothing, temperature changes, changes in degrees of hygrometry, pressure changes, or even attacks, for instance contact with certain chemical products which have or potentially have a very acidic, very basic or irritant nature, and with chemical products considered to be pollutants.

The skin is composed of layers of different tissues:
the epidermis, composed of keratinocytes, is its outermost part, followed by
the dermis, which is a connective tissue mainly composed of fibroblasts and of the extracellular matrix, and
the hypodermis, consisting of adipocytes, which is the deepest part and the part that is furthest from the external medium.

The skin performs various functions in the interest of the entire system that it shelters, among which the following may be recalled:
a mechanical barrier function to ensure the integrity of the internal medium of the body,
an emunctorial function directed toward secreting sweat based on water, salts and acidic waste,
a function of regulating the body temperature, and contains many other regulatory mechanisms, for instance its mechanism for adapting to and protecting against ultraviolet radiation (adaptive pigmentary coloring by producing melanin), for instance an immune monitoring system via the presence of macrophages and dendritic cells.

Human skin also constitutes the first image seen by others. Consequently, improving its appearance is a subject of constant concern for human beings. The skin is the reflection of a state of well-being, often associated with youthfulness, and, conversely, of a state of tiredness and/or aging. As a result, preserving and improving the state of the outermost layer of the skin, namely the epidermis, is a major focus for the research conducted by the cosmetics industries.

At the periphery of the epidermis is an upper cornified layer known as the *Stratum corneum*, which is the first layer of the epidermis to suffer the stresses of external origin, such as variations in external climatic conditions (temperature, pressure, hygrometry) or mechanical stresses.

The *Stratum corneum* is more particularly in contact with the cutaneous microbiota.

By "cutaneous microbiota" is meant, in the sense of the present patent application, a population of specialized or opportunistic microorganisms, examples being bacteria, fungi, yeasts, etc., which lives on the surface of the skin.

The cutaneous microbiota cannot be defined in a specific and generalized way for all individuals. Since the launch in 2007 of the "Human Microbiome Project" (HMP) of the National Institute of Health, researchers have been able to observe wide topographic variations in the human microbiota, and also large differences between individuals.

At least nineteen phyla have been identified, of which the four principal phyla are Actinobacteria (51.8%), Firmicutes (24.4%), Proteobacteria (16.5%) and Bacteroidetes (6.3%). The genera identified for the most part are *Corynebacterium, Propionibacterium,* and *Staphylococcus*. The abundance of each group is heavily dependent on the different locations. The fungal organisms isolated on the skin are of the genus *Malassezia* spp. In addition, acarids of the genus *Demodex* are also present and reside in the pilosebaceous units, usually those of the surface of the face.

This microbiota feeds both on molecules excreted by the skin (lipids, proteins, etc.) and on compounds secreted by the communities of microorganisms, demonstrating a true cooperation within this microbiota. Moreover, this relationship with the host constitutes a veritable symbiosis.

The bacteria may be commensal, when they live in contact with the cutaneomucosal coating of a host without giving rise to damage. An equilibrium is then established between the individual and the diverse commensal flora of the skin and the mucosae, but this equilibrium is constantly threatened by the physical or chemical attacks to which the *Stratum corneum* is subjected, such as for example pollution, temperature fluctuations, ultraviolet radiation, the intensive use of detergent surfactant products, stress, etc. Aside from these commensal bacteria, there are opportunistic, undesirable and/or pathogenic bacteria.

*Staphylococcus epidermidis* (*S. epidermidis*) makes up more than 90% of the resident aerobic flora present in the *Stratum corneum*. The resident flora is also made up of anaerobic bacteria belonging to the division of the Actinobacteria, such as *Propionibacterium acnes* (*P. acnes*), which is frequently encountered within sebaceous zones, such as for example the back, the face, and the scalp.

Whereas the normal flora of the skin constitutes a defense for the host, an increase or a reduction in the bacterial composition (dysbiosis) leads to skin inflammation and may be a cause of the development and visible manifestation of redness on the skin and/or the scalp, more particularly on sensitive and reactive skin.

Sensitive skin is defined by a particular reactivity of the skin. This skin reactivity is manifested conventionally in signs of discomfort, such as redness, in response to the subject being placed in contact with a trigger element, the origins of which may be various. The trigger may be the application of a cosmetic product at the surface of sensitive skin, the ingestion of food, exposure to sharp variations in temperature, to atmospheric pollution and/or to ultraviolet or infrared radiation. There are also associated factors such as the age and the type of skin. Accordingly, sensitive skin is more frequent among dry or greasy skin than among normal skin. The appearance of these signs of discomfort, which appear within the minutes following the contact of the subject with the trigger element, is one of the essential characteristics of sensitive skin. The signs involved are primarily dysesthetic sensations. Dysesthetic sensations are understood to be sensations with a greater or lesser degree of pain that are felt within a skin zone, such as prickling, tingling, itching, burning, hotness, discomfort, tightness, etc. It is nowadays known that these reactions of skin irritation and intolerance are linked in particular to inflammatory mechanisms.

SUMMARY OF THE INVENTION

In the sense of the present invention, sensitive skin encompasses irritable skin and intolerant skin.

Intolerant skin is skin which reacts via sensations of hotness, tightness, tingling and/or redness to various factors such as the application of cosmetic or dermatological products or of soap. Generally speaking, these signs are associated with erythema and with hyperseborrheic or acneic skin, or even rosaceiform skin, with or without dry patches.

Irritable skin is skin which reacts by a pruritus, in other words by itching or by prickling, to various factors such as the environment, emotions, foods, wind, rubbing, shaving, hard water with a high limestone concentration, fluctuations in temperature or humidity, or wool.

In the sense of the present invention, "sensitive" scalps have a more definite clinical semiology: the sensations of itching and/or prickling and/or hotness are essentially triggered by local factors such as rubbing, soap, surfactants, hard water with a high limestone concentration, shampoos or lotions. These sensations are also sometimes triggered by factors such as the environment, emotions and/or foods. Erythema and hyperseborrhea of the scalp and also a dandruff state are frequently associated with the aforesaid signs.

It is known that colonization of the pilosebaceous follicle by *P. acnes* is an important factor for the inflammatory response in common acne. In fact, acne is not in the strict sense an infectious disease, since this germ first exerts an inflammatory action, linked to its very numerous enzymatic and chemical secretions and to the immunological reactions to which it gives rise. Accordingly, *P. acnes* stimulates the production by the sebocytes, the keratinocytes and the leucocytes (lymphocytes and monocytes) of numerous inflammatory cytokines (IL-1α, IL1β, IL-6, IL-8, IL-10, IL-12, IL-17, IL-18, TNF-α, GM-CSF, and IFN-γ) and also of antimicrobial peptides (defensins and cathelicidins), of matrix metalloproteinases, of reactive oxygen species, and of other products implicated in the inflammatory response.

Moreover, *P. acnes* secretes a lipase which hydrolyzes the triglycerides of the sebum into free fatty acids, which are irritant and chemotactic for neutrophils.

The plant extracts which can be used for their actions on the human microbiota include a lyophilized extract of burdock leaves (or *Arctium lappa*), for which antibacterial activity has been demonstrated, and more particularly an activity against oral microorganisms, having been found to be most effective against bacteria associated with endodontic pathogens such as *Bacillus subtilis, Candida albicans, Lactobacillus acidophilus,* and *Pseudomonas aeruginosa* (1).

Burdock leaves are also described as being a possible topical remedy for skin problems such as eczema, acne, and psoriasis (1).

The literature also describes that the burdock leaf extracts show antimicrobial activities (2).

The Chinese patent application published under the number CN106074663 A describes a plant extract composition comprising a milo wood extract, a burdock root extract, and a honeysuckle extract, and describes more particularly that the burdock root extract treats dry skin, acute pruritus, inflammation, scars, and other symptoms, by inhibiting inflammatory factors induced by various causes (external stress or genetic factors), improving the immune activity and the antioxidant activity of the skin, and soothing and repairing the skin.

The U.S. patent application published under the number US20170136077 discloses that a certain number of plant extracts, including a burdock root extract, an *Epilobium angustifolium* root extract, and a *Cystoseira amentacea* extract, promote the reduction in the production of cytokines IL-8, IL-1 and TNF-α by keratinocytes stimulated with Phorbol 12-myristate 13-acetate (or "PMA").

This model is known for evaluating the antiinflammatory effect of ingredients, since PMA is an activator of the protein kinase C pathway, which has a general inflammatory effect on cells.

In the context of their research into new cosmetic active ingredients for preventing and/or treating signs of unesthetic effects linked to skin inflammation, such as, for example, redness on the skin and/or the scalp, more particularly on sensitive and reactive skin, the inventors endeavored to develop a new technical solution based on the use of a composition comprising polysubstituted quinic acids (or "PSQs"), on the use of burdock root extracts comprising said PSQs, obtained by a method comprising a prior step of aeroponic cultivation of said burdock, for producing moisturizing effects on the human skin.

In a first aspect, a subject of the invention is the use of a composition ($C_1$) for preventing or slowing the appearance of the unesthetic signs associated with inflammation of the skin and/or of the scalp, or else to eliminate them, with the composition (C1) comprising, per 100% of its mass:
   a)—from 60.0% by mass to 75.0% by mass of an organic solvent ($SO_1$) selected from 1,2-propanediol, 1,3-propanediol, 1,4-butanediol, 1,3-butanediol, 1,2-butanediol, 2-methyl-2,4-pentanediol, 1,6-hexanediol, 1,8-octanediol, or a mixture of these compounds;
   b)—from 0.1% by mass to 2.0% by mass of a composition (ES) comprising a mass quantity $x_1$, expressed as mass equivalents of 1-O-(2-caffeoyl)maloyl-3,5-O-dicaffeoylquinic acid, of greater than or equal to 200 mg/g of at least one compound of general formula (I):

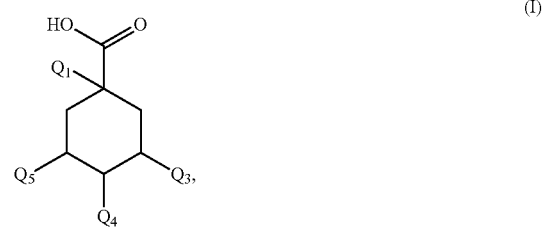

in which $Q_1$, $Q_2$, $Q_3$, $Q_4$ and $Q_5$ independently of one another represent the hydroxyl radical or a salt thereof or a radical selected from:

(i)—the caffeoyl radical of formula II:

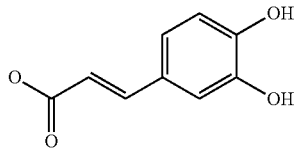
(II)

(ii)—the maloyl radical of formula (IIIa) or (IIIb):

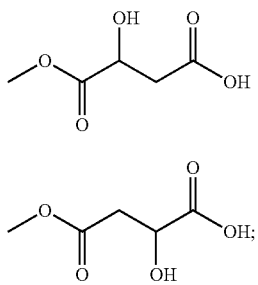
(IIIa)

(IIIb)

(iii)—the caffeoyl maloyl radical of formula (IVa) or (IVb):

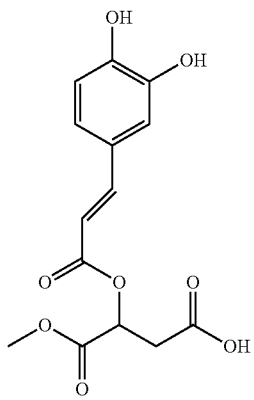
(IVa)

(IVb)

(iv)—the maloyl caffeoyl radical of formula (Va), (Vb), (Vc) or (Vd),

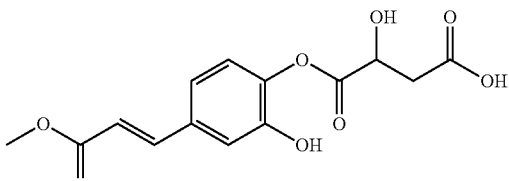
(Va)

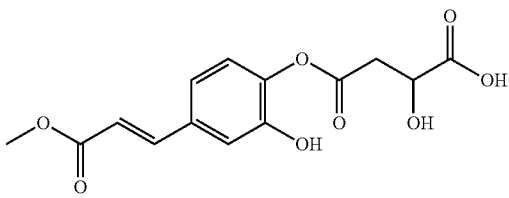
(Vb)

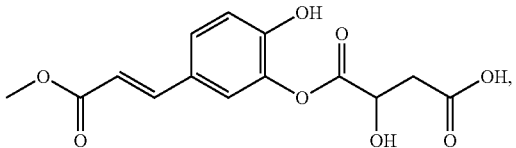
(Vc)

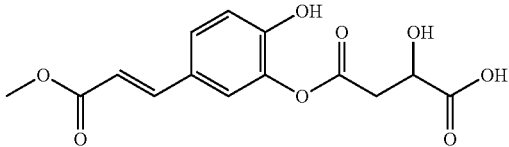
(Vd)

with the proviso that at least one of these radicals $Q_1$, $Q_2$, $Q_3$, $Q_4$ and $Q_5$ represents neither the —OH radical nor a salt thereof; and c)—from 20.0% by mass to 35.0% by mass of water.

In the sense of the present invention, "unesthetic signs associated with inflammation of the skin and/or the scalp" is understood to mean, in the sense of the invention, any modifications to the external appearance of the skin or the scalp that are due to inflammation of said skin or said scalp, such as for example the inflammation manifesting in the form of redness of the skin and/or the scalp.

In the sense of the present invention, the expression "said mass quantity $x_1$ being expressed as mass equivalents of 1-O-(2-caffeoyl)maloyl-3,5-O-dicaffeoylquinic acid" means that the mass quantity $x_1$ was determined by using a quantitative analytical UHPLC-MS method (Ultra High Performance Liquid Chromatography-Mass Spectra), using as reference standard a standard sample of 1-O-(2-caffeoyl) maloyl-3,5-O-dicaffeoylquinic acid isolated beforehand and purified to a content of greater than or equal to 99%.

This kind of quantitative UHPLC-MS analysis was performed using a Shimadzu_Nexera_LCMS 2020 UHPLC-MS apparatus, equipped with a diode array detector and adjusted to a wavelength of 330 nanometers, with a Kinetex 2.6µ XB-C18 100A. 100×2.1 column, and employing a mobile phase A composed of water and 0.1% by mass of formic acid and a mobile phase consisting of acetonitrile.

The compounds of general formula (I) present in the composition (ES) include the following:

the compounds of the class of DiCaffeoylQuinic acids (DCQs) as described in table 1 below:

TABLE 1

DiCaffeoylQuinic acids (DCQs)

| Q1 | Q3 | Q4 | Q5 |
|---|---|---|---|
| 1,3-O-Dicaffeoylquinic acid (1,3-DCQ) | | | |
| Caffeoyl | Caffeoyl | OH | OH |
| 1,4-O-Dicaffeoylquinic acid (1,4-DCQ) | | | |
| Caffeoyl | OH | Caffeoyl | OH |
| 1,5-O-Dicaffeoylquinic acid (1,5-DCQ) | | | |
| Caffeoyl | OH | OH | Caffeoyl |
| 3,4-O-Dicaffeoylquinic acid (3,4-DCQ) | | | |
| OH | Caffeoyl | Caffeoyl | OH |
| 3,5-O-Dicaffeoylquinic acid (3,5-DCQ) | | | |
| OH | Caffeoyl | OH | Caffeoyl |
| 4,5-O-Dicaffeoylquinic acid (4,5 DCQ) | | | |
| OH | OH | Caffeoyl | Caffeoyl | the compounds of the class of TdCaffeoylQuinic acids (TCQs) as described in table 2 below:

TABLE 2

TriCaffeoylQuinic acid (TCQ)

| Q1 | Q3 | Q4 | Q5 |
|---|---|---|---|
| 1,3,4-O-Tricaffeoylquinic acid (1,3,4-TCQ) | | | |
| Caffeoyl | Caffeoyl | Caffeoyl | OH |
| 1,3,5-O-Tricaffeoylquinic acid (1,3,5-TCQ) | | | |
| Caffeoyl | Caffeoyl | OH | Caffeoyl |
| 1,4,5-O-Tricaffeoylquinic acid (1,4,5-TCQ) | | | |
| Caffeoyl | OH | Caffeoyl | Caffeoyl |
| 3,4,5-O-Tricaffeoylquinic acid (1,3,4-TCQ) | | | |
| OH | Caffeoyl | Caffeoyl | Caffeoyl | the compounds of the class of Maloyl TriCaffeoylQuinic acids (m-TCQs) as described in table below:

TABLE 3

Maloyl TriCaffeoylQuinic (m-TCQs)

| Q1 | Q3 | Q4 | Q5 |
|---|---|---|---|
| 1-O-Maloyl(3,4,5-O-tricaffeoyl)quinic acid | | | |
| Maloyl | Caffeoyl | Caffeoyl | Caffeoyl |
| 3-O-Maloyl(1,4,5-O-tricaffeoyl)quinic acid | | | |
| Caffeoyl | Maloyl | Caffeoyl | Caffeoyl |
| 4-O-Maloyl(1,3,5-O-tricaffeoyl)quinic acid | | | |
| Caffeoyl | Caffeoyl | Maloyl | Caffeoyl |
| 5-O-Maloyl(1,3,4-O-tricaffeoyl)quinic acid | | | |
| Caffeoyl | Caffeoyl | Caffeoyl | Maloyl | the compounds of the class of Maloyl DiCaffeoylQuinic acids (m-DCQs) as described in table 4 below:

TABLE 4

Maloyl DiCaffeoylQuinic acid (m-DCQ)

| Q1 | Q3 | Q4 | Q5 |
|---|---|---|---|
| 4-O-Maloyl(1,3-O-dicaffeoyl)quinic acid | | | |
| Caffeoyl | Caffeoyl | Maloyl | OH |
| 5-O-Maloyl(1,3-O-dicaffeoyl)quinic acid | | | |
| Caffeoyl | Caffeoyl | OH | Maloyl |
| 3-O-Maloyl(1,4-O-dicaffeoyl)quinic acid | | | |
| Caffeoyl | Maloyl | Caffeoyl | OH |
| 5-O-Maloyl(1,4-O-dicaffeoyl)quinic acid | | | |
| Caffeoyl | OH | Caffeoyl | Maloyl |
| 3-O-Maloyl(1,5-O-dicaffeoyl)quinic acid | | | |
| Caffeoyl | Maloyl | OH | Caffeoyl |
| 4-O-Maloyl(1,5-O-dicaffeoyl)quinic acid | | | |
| Caffeoyl | OH | Maloyl | Caffeoyl |
| 1-O-Maloyl(3,4-O-dicaffeoyl)quinic acid | | | |
| Maloyl | Caffeoyl | Caffeoyl | OH |
| 5-O-Maloyl(3,4-O-dicaffeoyl)quinic acid | | | |
| OH | Caffeoyl | Caffeoyl | Maloyl |
| 1-O-Maloyl(3,5-O-dicaffeoyl)quinic acid | | | |
| Maloyl | Caffeoyl | OH | Caffeoyl |
| 4-O-Maloyl(3,5-O-dicaffeoyl)quinic acid | | | |
| OH | Caffeoyl | Maloyl | Caffeoyl |
| 1-O-Maloyl(4,5-O-dicaffeoyl)quinic acid | | | |
| Maloyl | OH | Caffeoyl | Caffeoyl |
| 3-O-Maloyl(4,5-O-dicaffeoyl)quinic acid | | | |
| OH | Maloyl | Caffeoyl | Caffeoyl | the compounds of the class of CafeoylMaloyl Tri-CaffeoylQuinic acids as descried in table 5 below:

TABLE 5

CaffeoylMaloyl TriCaffeoylQuinic acid (cm-TCQ)

| Q1 | Q3 | Q4 | Q5 |
|---|---|---|---|
| 1-O-(2-Caffeoylmaloyl)-(3,4,5-O-tricaffeoyl)quinic acid | | | |
| CaffeoylMaloyl | Caffeoyl | Caffeoyl | Caffeoyl |
| 3-O-(2-Caffeoylmaloyl)-(1,4,5-O-tricaffeoyl)quinic acid | | | |
| Caffeoyl | CaffeoylMaloyl | Caffeoyl | Caffeoyl |
| 4-O-(2-Caffeoylmaloyl)-(1,3,5-O-tricaffeoyl)quinic acid | | | |
| Caffeoyl | Caffeoyl | CaffeoylMaloyl | Caffeoyl |
| 5-O-(2-Caffeoylmaloyl)-(1,3,4-O-tricaffeoyl)quinic acid | | | |
| Caffeoyl | Caffeoyl | Caffeoyl | CaffeoylMaloyl | the compounds of the class of CaffeoylMaloyl DiCaffeoyl Quinic acids as described in table 6 below:

TABLE 6

CaffeoylMaloyl DiCaffeoylQuinic acid (cm-DCQ)

| Q1 | Q3 | Q4 | Q5 |
|---|---|---|---|
| 4-O-(2-Caffeoyl)maloyl (1,3-O-dicaffeoyl)quinic acid | | | |
| Caffeoyl | Caffeoyl | CaffeoylMaloyl | OH |
| 5-O-(2-Caffeoyl)maloyl (1,3-O-dicaffeoyl)quinic acid | | | |
| Caffeoyl | Caffeoyl | OH | CaffeoylMaloyl |
| 3-O-(2-Caffeoyl)maloyl-(1,4-O-dicaffeoyl)quinic acid | | | |
| Caffeoyl | CaffeoylMaloyl | Caffeoyl | OH |
| 5-O-(2-Caffeoyl)maloyl-(1,4-O-dicaffeoyl)quinic acid | | | |
| Caffeoyl | OH | Caffeoyl | CaffeoylMaloyl |
| 3-O-(2-Caffeoyl)maloyl-(1,5-O-dicaffeoyl)quinic acid | | | |
| Caffeoyl | CaffeoylMaloyl | OH | Caffeoyl |
| 4-O-(2-Caffeoyl)maloyl-(1,5-O-dicaffeoyl)quinic acid | | | |
| Caffeoyl | OH | CaffeoylMaloyl | Caffeoyl |
| 1-O-(2-Caffeoyl)maloyl-(3,4-O-dicaffeoyl)quinic acid | | | |
| CaffeoylMaloyl | Caffeoyl | Caffeoyl | OH |
| 5-O-(2-Caffeoyl)maloyl-(3,4-O-dicaffeoyl)quinic acid | | | |
| OH | Caffeoyl | Caffeoyl | CaffeoylMaloyl |
| 1-O-(2-Caffeoyl)maloyl-(3,5-O-dicaffeoyl)quinic acid | | | |
| Maloyl | Caffeoyl | OH | Caffeoyl |
| 4-O-(2-Caffeoyl)maloyl-(3,5-O-dicaffeoyl)quinic acid | | | |
| OH | Caffeoyl | CaffeoylMaloyl | Caffeoyl |
| 1-O-(2-Caffeoyl)maloyl-(4,5-O-dicaffeoyl)quinic acid | | | |
| CaffeoylMaloyl | OH | Caffeoyl | Caffeoyl |
| 3-O-(2-Caffeoyl)maloyl-(4,5-O-dicaffeoyl)quinic acid | | | |
| OH | CaffeoylMaloyl | Caffeoyl | Caffeoyl |

In one particular aspect of the present invention, the composition (ES) as defined above comprises at least:
  at least one compound of formula (Ia) corresponding to the formula (I) for which $Q_1$ represents the maloyl radical of formula (IIIa) or of formula (IIIb) and $Q_3$ and $Q_4$ and $Q_5$ are identical and each represent the caffeoyl radical of formula (II);
  a compound of formula (Ib), corresponding to the formula (I) for which $Q_1$ represents the caffeoylmaloyl radical of formula (IVa) or of formula (IVb), $Q_3$ and $Q_5$ each represent the caffeoyl radical of formula (II), and $Q_4$ represents the hydroxyl radical, and
  at least one compound of formula (Ic) selected from:
    the compound of formula $(Ic_1)$, corresponding to the formula (I) for which $Q_1$ and $Q_5$ each represent the caffeoyl radical of formula (II), $Q_3$ represents the hydroxyl radical, and $Q_4$ represents the caffeoylmaloyl radical of formula (IVa) or of formula (IVb); and
    the compound of formula $(Ic_2)$, corresponding to the formula (I) for which $Q_1$ and $Q_4$ represent the caffeoyl radical of formula (II), $Q_3$ represents the hydroxyl radical, and $Q_5$ represents the caffeoylmaloyl radical of formula (IVa) or of formula (IVb).

In a more particular aspect of the present invention, in the composition (ES) as defined above, the compound of formula (Ia) corresponding to the formula (I) as defined above and for which $Q_1$ represents the maloyl radical of formula (IIIa), $Q_3$ and $Q_4$ and $Q_5$ are identical and represent the caffeoyl radical of formula (II).

In a more particular aspect of the present invention, in the composition (ES) as defined above, the compound of formula (Ia) corresponding to the formula (I) as defined above and for which $Q_1$ represents the maloyl radical of formula (IIIb), $Q_3$ and $Q_4$ and $Q_5$ are identical and represent the caffeoyl radical of formula (II).

In a more particular aspect of the present invention, in the composition (ES) as defined above, the compound of formula (Ib) corresponding to the formula (I) as defined above and for which $Q_1$ represents the caffeoylmaloyl radical of formula (IVa); $Q_3$ and $Q_5$ are identical and represent the caffeoyl radical of formula (II); $Q_4$ represents the —OH radical.

In a more particular aspect of the present invention, in the composition (ES) as defined above, the compound of formula (Ib) corresponding to the formula (I) as defined above and for which $Q_1$ represents the caffeoylmaloyl radical of formula (IVb); $Q_1$ and $Q_5$ are identical and represent the caffeoyl radical of formula (II); $Q_4$ represents the —OH radical.

In a more particular aspect of the present invention, in the composition (ES) as defined above, the compound of formula (Ic) is the compound of formula $(Ic_1)$, corresponding to the formula (I) as defined above and for which $Q_1$ and $Q_5$ are identical and represent the caffeoyl radical of formula (II); $Q_3$ represents the —OH radical; 04 represents the caffeoylmaloyl radical of formula (IVa).

In a more particular aspect of the present invention, in the composition (ES) as defined above, the compound of formula (Ic) is the compound of formula $(Ic_1)$, corresponding to the formula (I) as defined above and for which $Q_1$ and $Q_5$ are identical and represent the caffeoyl radical of formula (II); $Q_3$ represents the —OH radical; $Q_4$ represents the caffeoylmaloyl radical of formula (IVb).

In a more particular aspect of the present invention, in the composition (ES) as defined above, the compound of formula (Ic) is the compound of formula $(Ic_2)$, corresponding to the formula (I) as defined above and for which $Q_1$ and $Q_4$ are identical and represent the caffeoyl radical of formula (II); $Q_3$ represents the —OH radical; $Q_5$ represents the caffeoylmaloyl radical of formula (IVa).

In a more particular aspect of the present invention, in the composition (ES) as defined above, the compound of formula (Ic) is the compound of formula $(Ic_2)$, corresponding to the formula (I) as defined above and for which $Q_1$ and $Q_4$ are identical and represent the caffeoyl radical of formula (II); $Q_3$ represents the —OH radical; $Q_5$ represents the caffeoylmaloyl radical of formula (Vb).

In a more particular aspect of the present invention, the composition (ES) as defined above comprises at least:
  a compound of formula (Ia) as defined above for which $Q_1$ represents the maloyl radical of formula (IIIa) or the maloyl radical of formula (IIIb), and
  a compound of formula (Ib) as defined above and for which $Q_1$ represents the caffeoylmaloyl radical of formula (IVa) or the caffeoylmaloyl radical of formula (Vb), and
  a compound of formula $(Ic_1)$ as defined above and for which $Q_4$ represents the caffeoylmaloyl radical of formula (IVa) or the caffeoylmaloyl radical of formula (Vb).

In a more particular aspect of the present invention, the composition (ES) as defined above comprises at least:
  a compound of formula (Ia) as defined above for which $Q_1$ represents the maloyl radical of formula (IIIa) or the maloyl radical of formula (IIIb), and a compound of formula (Ib) as defined above and for which $Q_1$ represents the caffeoylmaloyl radical of formula (IVa) or the caffeoylmaloyl radical of formula (Vb), and a compound of formula ($Ic_2$) as defined above and for which $Q_5$ represents the caffeoylmaloyl radical of formula (IVa) or of formula (IVb).

In one particular aspect of the present invention, the organic solvent ($SO_1$) present in the composition (C1) as defined above is selected from the elements of the group consisting of 1,2-propanediol, 1,3-propanediol, and 2-methyl-2,4-pentanediol.

In another particular aspect of the present invention, the composition ($C_1$) comprises, per 100% of its mass:
- from 60.0% by mass to 75.0% by mass of 1,2-propanediol,
- from 0.1% by mass to 2.0% by mass of a composition (ES) comprising a mass quantity $x_1$, expressed as mass equivalents of 1-O-(2-caffeoyl)maloyl-3,5-O-dicaffeoylquinic acid, of greater than or equal to 200 mg/of at least the compound of formula (Ia) as defined in claim 2, and of at least the compound of formula (Ib) as defined in claim 2, and of at least the compound of formula (Ic) as defined in claim 2
- from 20.0% by mass to 35.0% by mass of water.

The composition (C1) used in the context of the present invention may be prepared by simple mixing of its constituents, at a temperature of between 20° C. and 60° C., more particularly between 20° C. and 40° C., and more particularly still between 20° C. and 30° C., and with anchor-type mechanical stirring at a speed of between 50 revolutions/minute and 150 revolutions/minute.

More specifically, the composition (C1) used in the context of the invention may be prepared by a method comprising the following successive steps:
- a step a) of cultivating the plant *Arctium lappa* under soilless conditions, fed with a nutrient solution, to give a biomass ($BM_1$);
- a step b) of immersing the roots of said biomass ($BM_1$) obtained in step a) above in a medium ($S_1$), such that the biomass ($BM_1$)/mixture ($S_1$) ratio is between 0.5 kg/L and 1.5 kg/L, said medium ($S_1$) comprising, per 100% of its own mass, from 20% to 35% by mass of water, the pH of which has been adjusted to a value of between 1.5 and 3.5 by addition of a protic acid selected from sulfuric acid, phosphoric acid and hydrochloric acid, and from 65% to 80% by mass of an organic solvent ($SO_1$) selected from 1,2-propanediol, 1,3-propanediol, 1,4-butanediol, 1,3-butanediol, 1,2-butanediol, 2-methyl-2,4-pentanediol, 1,6-hexanediol, 1,8-octanediol or a mixture of these diols;
- a step c) of separating the roots of the biomass at the end of the treatment defined in step b), to isolate a liquid phase (L);
- a step d) of immersing said biomass ($BM_2$) obtained from step c) in said medium ($S_1$), in a biomass ($BM_2$)/mixture (S) ratio of between 0.1 kg/L and 1.5 kg/L;
- a step e) of separating said biomass ($BM_2$) at the end of the treatment defined in step d), to isolate a liquid phase ($L_2$);
- a step f) of filtering said liquid phase ($L_3$) obtained in step d), to isolate a liquid liquid phase ($L_3$);
- a step g) of mixing said liquid phases ($L_1$) and (La), then, if necessary, adding water and/or said organic solvent ($SO_1$), so as to obtain the expected composition ($C_1$).

The step a) of cultivating the plant *Arctium lappa* under soilless conditions (or so-called aeroponic conditions) takes place according to the standard conditions known to the skilled person, and more particularly those relating to the effect of the nitrogen content (2) (3) (4) (5) (6) and of the phosphorous and potassium content present in the culture medium. The step a) of cultivating under soilless conditions therefore takes place with optimization of the nitrogen/phosphorous/potassium ratio present in the nutrient medium, and with optimization of the electroconductivity parameter of such a nutrient medium.

Step a) is generally carried out at a temperature of between 20° C. and 40° C. for a time of between 4 and 10 weeks, so as to give a biomass ($BM_1$), in a substantial quantity particularly in terms of the roots; step a) is halted when the biomass ($BM_1$) is no longer observed to grow.

A further subject of the present invention is a method for preventing or for slowing the appearance of the unesthetic signs associated with inflammation of the skin and/or of the scalp, or else to eliminate them, characterized in that it comprises at least one step a) of applying, to the surface of the skin to be treated, an effective amount of a topical-use composition ($C_2$) comprising at least one cosmetically acceptable excipient (E) and a composition ($C_1$) consisting, per 100% of its mass, of:
a) from 60.0% by mass to 75.0% by mass of 1,2-propanediol,
b) from 0.1% by mass to 2.0% by mass of a composition (ES) comprising a mass quantity $x_1$, expressed as mass equivalents of 1-O-(2-caffeoyl)maloyl-3,5-O-dicaffeoylquinic acid, of greater than or equal to 200 mg/of at least the compound of formula (Ia) as defined in claim 2, and of at least the compound of formula (Ib) as defined in claim 2, and of at least the compound of formula (Ic) as defined in claim 2
c) from 20.0% by mass to 35.0% by mass of water.

By "effective amount" is meant, in the definition of the method as defined above, an amount such that it allows the reduction in the intensity, or the slowing-down of the appearance, or the elimination, of the unesthetic signs associated with inflammation of the skin and/or of the scalp, and more particularly of redness. Generally speaking, the amount used will be about 1 gram to 5 grams of a topical-use composition ($C_2$) as defined above.

The expression "for topical use" or "topical-use" as used in the definition of the composition ($C_2$) which is a subject of the present invention means that said composition ($C_2$) is employed by application to the skin, whether by direct application or by indirect application when said composition ($C_2$) according to the invention is impregnated onto a support intended to be brought into contact with the skin (paper, wipe, textile, transdermal device, etc.).

Said composition ($C_2$) is generally spread over the surface of the skin to be treated, after which the skin is massaged for a short while.

The expression "cosmetically acceptable" used in the definition of the composition ($C_2$) which is a subject of the present invention means, according to Council of the European Economic Community Directive No. 76/768/EEC of Jul. 27, 1976, amended by Directive No. 93/35/EEC of Jun. 14, 1993, that it includes any substance or preparation intended to be brought into contact with the various parts of the human body (epidermis, body hair and head hair system, nails, lips and genitals) or with the teeth and mucous membranes of the mouth, for the purpose, exclusively and mainly, of cleansing them, fragrancing them, modifying the appearance thereof and/or correcting body odors thereof and/or protecting them or keeping them in good condition.

The composition ($C_2$) for topical use that is a subject of the present invention is generally in the form of an aqueous or aqueous-alcoholic or aqueous-glycolic solution, in the form of a suspension, an emulsion, a microemulsion or a nanoemulsion, whether of water-in-oil, oil-in-water, water-in-oil-in-water or oil-in-water-in-oil type, or in the form of a powder.

The composition ($C_2$) for topical use that is a subject of the present invention can be packaged in a bottle, in a device of "pump bottle" type, in pressurized form in an aerosol device, in a device equipped with a perforated wall, such as a grill, or in a device equipped with a ball applicator (known as a "roll-on").

In general, the composition ($C_2$) for topical use that is a subject of the present invention also comprise excipients and/or active principles that are commonly employed in the field of formulations for topical use, especially cosmetic, dermocosmetic, pharmaceutical or dermopharmaceutical formulations, such as thickening and/or gelling surfactants, stabilizers, film-forming compounds, hydrotropic agents, plasticizing agents, emulsifying and coemulsifying agents, opacifying agents, pearlescent agents, superfatting agents, sequesterants, chelating agents, antioxidants, fragrances, preservatives, conditioning agents, whitening agents intended for bleaching body hairs and the skin, active principles intended to provide a treating action with regard to the skin or hair, sunscreens, inorganic fillers or pigments, particles imparting a visual effect or intended for the encapsulation of active agents, exfoliating particles or texturing agents.

As examples of foaming and/or detergent surfactants that may be combined with the composition ($C_1$), mention may be made of anionic, cationic, amphoteric or nonionic foaming and/or detergent surfactants.

Among the anionic foaming and/or detergent surfactants which may be combined with the composition ($C_1$), mention may be made of alkali metal, alkaline earth metal, ammonium, amine or amino alcohol salts of alkyl ether sulfates, of alkyl sulfates, of alkylamido ether sulfates, of alkylaryl polyether sulfates, of monoglycerides sulfates, of α-olefinsulfonates, of paraffinsulfonates, of alkyl phosphates, of alkyl ether phosphates, of alkylsulfonates, of alkylamidesulfonates, of alkylarylsulfonates, of alkylcarboxylates, of alkyl sulfosuccinates, of alkyl ether sulfosuccinates, of alkylamide sulfosuccinates, of alkyl sulfoacetates, of alkylsarcosinates, of acylisethionates, of N-acyltaurates, of acyl lactylates, of N-acylated derivatives of amino acids, of N-acylated derivatives of peptides, of N-acylated derivatives of proteins or of N-acylated derivatives of fatty acids.

Among the amphoteric foaming and/or detergent surfactants which may be combined with the composition ($C_1$), mention may be made of alkylbetaines, alkylamidobetaines, sultaines, alkylamidoalkylsulfobetaines, imidazoline derivatives, phosphobetaines, amphopolyacetates and amphopropionates.

Among the cationic foaming and/or detergent surfactants that may be combined with the composition ($C_1$), mention may be made particularly of quaternary ammonium derivatives.

Among the nonionic foaming and/or detergent surfactants that may be combined with the composition ($C_1$), mention may be made more particularly of alkylpolyglycosides including a linear or branched, saturated or unsaturated aliphatic radical, including from 8 to 16 carbon atoms, for instance octyl polyglucoside, decyl polyglucoside, undecylenyl polyglucoside, dodecyl polyglucoside, tetradecyl polyglucoside, hexadecyl polyglucoside, 1,12-dodecanediyl polyglucoside; ethoxylated hydrogenated castor oil derivatives, for instance the product sold under the INCI name PEG-40 hydrogenated castor oil; polysorbates, for instance Polysorbate 20, Polysorbate 40, Polysorbate 60, Polysorbate 70, Polysorbate 80 and Polysorbate 85; coconut kernel amides; N-alkylamines.

As examples of thickening and/or gelling surfactants that may be combined with the composition ($C_1$), mention may be made of optionally alkoxylated fatty alkylpolyglycoside esters, such as ethoxylated methylpolyglucoside esters such as PEG 120 methyl glucose trioleate and PEG 120 methyl glucose dioleate, sold respectively under the names GLUCAMATE™ LT and GLUMATE™ DOE120; alkoxylated fatty esters such as PEG 150 pentaerythrityl tetrastearate, sold under the name CROTHIX™ DS53, PEG 55 propylene glycol oleate, sold under the name ANTIL™ 141; polyalkylene glycol carbamates with fatty chains such as PPG-14 laureth isophoryl dicarbamate, sold under the name ELFACOS™ T211, and PPG-14 palmeth-60 hexyl dicarbamate, sold under the name ELFACOS™ GT2125.

As examples of thickening and/or gelling agents that may be combined with the composition ($C_1$), mention may be made of copolymers of AMPS and alkyl acrylates in which the carbon chain comprises between four and thirty carbon atoms and more particularly between ten and thirty carbon atoms, linear, branched or crosslinked terpolymers of at least one monomer possessing a free, partially salified or totally salified strong acid function with at least one neutral monomer and at least one monomer of formula (VIII):

$$CH_2=C(R'_3)-C(=O)-[CH_2-CH_2-O]n'-R'_4 \quad (VIII)$$

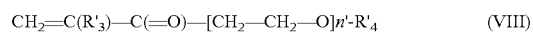

in which $R'_3$ represents a hydrogen atom or a methyl radical, $R'_4$ represents a linear or branched alkyl radical containing from eight to thirty carbon atoms, and n' represents a number greater than or equal to one and less than or equal to fifty.

As examples of thickening and/or gelling agents that may be combined with the composition ($C_1$), mention may be made of polysaccharides consisting only of monosaccharides, such as glucans or glucose homopolymers, glucomannoglucans, xyloglycans, galactomannans of which the degree of substitution (DS) of the D-galactose units on the main D-mannose chain is between 0 and 1, and more particularly between 1 and 0.25, such as galactomannans originating from cassia gum (DS=1/5), locust bean gum (DS=1/4), tara gum (DS=1/3), guar gum (DS=1/2) or fenugreek gum (DS=1).

As examples of thickening and/or gelling agents which may be combined with the composition ($C_1$), mention may be made of polysaccharides consisting of monosaccharide derivatives, such as sulfated galactans and more particularly carrageenans and agar, uronans and more particularly algins, alginates and pectins, heteropolymers of monosaccharides and uronic acids and more particularly xanthan gum, gellan gum, gum arabic exudates and karaya gum exudates, glucosaminoglycans.

As examples of thickening and/or gelling agents that may be combined with the composition ($C_1$), mention may be made of cellulose, cellulose derivatives such as methylcellulose, ethylcellulose, hydroxypropylcellulose, silicates, starch, hydrophilic starch derivatives, and polyurethanes.

As examples of stabilizing agents that may be combined with the composition ($C_1$), mention may be made of monocrystalline waxes, and more particularly ozokerite, mineral salts such as sodium chloride or magnesium chloride, silicone polymers such as polysiloxane polyalkyl polyether copolymers.

As examples of solvents that may be combined with the composition ($C_1$), mention may be made of water, organic solvents such as glycerol, diglycerol, glycerol oligomers, ethylene glycol, propylene glycol, butylene glycol, 1,3-propanediol, 1,2-propanediol, hexylene glycol, diethylene glycol, xylitol, erythritol, sorbitol, water-soluble alcohols such as ethanol, isopropanol or butanol, and mixtures of water and of said organic solvents.

As examples of spring or mineral waters that may be combined with the composition ($C_1$), mention may be made of spring or mineral waters having a mineralization of at least 300 mg/I, in particular Avene water, Vittel water, Vichy basin waters, Uriage water, La Roche Posay water, La Bourboule water, Enghien-les-bains water, Saint-Gervais-les-bains water, Néris-les-bains water, Allevard-les-bains water, Digne water, Maizieres water, Neyrac-les-bains water, Lons le Saunier water, Rochefort water, Saint Christau water, Fumades water and Tercis-les-bains water.

As examples of hydrotropic agents that may be combined with the composition ($C_1$), mention may be made of xylene sulfonates, cumene sulfonates, hexyl polyglucoside, 2-ethylhexyl polyglucoside and n-heptyl polyglucoside.

As examples of emulsifying surfactants that may be combined with the composition ($C_1$), mention may be made of nonionic surfactants, anionic surfactants and cationic surfactants.

As examples of emulsifying nonionic surfactants that may be combined with the composition ($C_1$), mention may be made of fatty acid esters of sorbitol, for instance the products sold under the names Montane™ 40, Montane™ 60, Montane™ 70, Montane™ 80 and Montane™ 85; compositions comprising glyceryl stearate and stearic acid ethoxylated with between 5 mol and 150 mol of ethylene oxide, for instance the composition comprising stearic acid ethoxylated with 135 mol of ethylene oxide and glyceryl stearate sold under the name Simulsol™ 165; mannitan esters; ethoxylated mannitan esters; sucrose esters; methyl glucoside esters; alkyl polyglycosides including a linear or branched, saturated or unsaturated aliphatic radical including from 14 to 36 carbon atoms, for instance tetradecyl polyglucoside, hexadecyl polyglucoside, octadecyl polyglucoside, hexadecyl polyxyloside, octadecyl polyxyloside, eicosyl polyglucoside, dodecosyl polyglucoside, (2-octydodecyl) polyxyloside, (12-hydroxystearyl) polyglucoside; compositions of linear or branched, saturated or unsaturated fatty alcohols including from 14 to 36 carbon atoms and of alkyl polyglycosides as described previously, for example the compositions sold under the names Montanov™ 68, Montanov™ 14, Montanov™ 82, Montanov™ 202, Montanov™ S, Montanov™ WO18, Montanov™ L, Fluidanov™ 20X and Easynov™.

As examples of anionic surfactants that may be combined with the composition ($C_1$), mention may be made of glyceryl stearate citrate, cetearyl sulfate, soaps such as sodium stearate or triethanolammonium stearate, and N-acylated derivatives of salified amino acids, for instance stearoyl glutamate.

As examples of emulsifying cationic surfactants that may be combined with the composition ($C_1$), mention may be made of amine oxides, quaternium-82 and the surfactants described in patent application WO96/00719 and mainly those in which the fatty chain comprises at least 16 carbon atoms.

As examples of opacifying and/or pearlescent agents that may be combined with the composition ($C_1$), mention may be made of sodium palmitate, sodium stearate, sodium hydroxystearate, magnesium palmitate, magnesium stearate, magnesium hydroxystearate, ethylene glycol monostearate, ethylene glycol distearate, polyethylene glycol monostearate, polyethylene glycol distearate and fatty alcohols including from 12 to 22 carbon atoms.

As examples of texturing agents that may be combined with the composition ($C_1$), mention may be made of N-acylated derivatives of amino acids, such as lauroyl lysine sold under the name Aminohope™LL, octenyl starch succinate sold under the name Dryflo™, myristyl polyglucoside sold under the name Montanov™ 14, cellulose fibers, cotton fibers, chitosan fibers, talc, sericite and mica.

As examples of deodorant agents that may be combined with the composition ($C_1$), mention may be made of alkali metal silicates, zinc salts, such as zinc sulfate, zinc gluconate, zinc chloride or zinc lactate; quaternary ammonium salts, such as cetyltrimethylammonium salts or cetylpyridinium salts; glycerol derivatives, such as glyceryl caprate, glyceryl caprylate or polyglyceryl caprate; 1,2-decanediol; 1,3-propanediol; salicylic acid; sodium bicarbonate; cyclodextrins; metal zeolites; Triclosan™; aluminum bromohydrate, aluminum chlorohydrates, aluminum chloride, aluminum sulfate, aluminum zirconium chlorohydrates, aluminum zirconium trichlorohydrate, aluminum zirconium tetrachlorohydrate, aluminum zirconium pentachlorohydrate, aluminum zirconium octachlorohydrate, aluminum sulfate, sodium aluminum lactate, or complexes of aluminum chlorohydrate and of glycol, such as the aluminum chlorohydrate and propylene glycol complex, the aluminum dichlorohydrate and propylene glycol complex, the aluminum sesquichlorohydrate and propylene glycol complex, the aluminum chlorohydrate and polyethylene glycol complex, the aluminum dichlorohydrate and polyethylene glycol complex or the aluminum sesquichlorohydrate and polyethylene glycol complex.

As examples of oils that may be combined with the composition ($C_1$), mention may be made of mineral oils such as liquid paraffin, liquid petroleum jelly, isoparaffins or white mineral oils; oils of animal origin, such as squalene or squalane; plant oils, such as phytosqualane, sweet almond oil, coconut kernel oil, castor oil, jojoba oil, olive oil, rapeseed oil, groundnut oil, sunflower oil, wheat germ oil, corn germ oil, soybean oil, cotton oil, alfalfa oil, poppy oil, pumpkin oil, evening primrose oil, millet oil, barley oil, rye oil, safflower oil, candlenut oil, passionflower oil, hazelnut oil, palm oil, shea butter, apricot kernel oil, beauty-leaf oil, sisymbrium oil, avocado oil, calendula oil, oils derived from flowers or vegetables, ethoxylated plant oils; synthetic oils, for instance fatty acid esters such as butyl myristate, propyl myristate, isopropyl myristate, cetyl myristate, isopropyl palmitate, octyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate, isocetyl lanolate, fatty acid monoglycerides, diglycerides and triglycerides, for instance glyceryl triheptanoate, alkylbenzoates, hydrogenated oils, poly(α-olefins), polyolefins such as poly(isobutane), synthetic isoalkanes, for instance isohexadecane, isododecane, perfluorinated oils; silicone oils, for instance dimethylpolysiloxanes, methylphenylpolysiloxanes, silicones modified with amines, silicones modified with fatty acids, silicones modified with alcohols, silicones modified with alcohols and fatty acids, silicones modified with polyether groups, epoxy-modified silicones, silicones modified with fluoro groups, cyclic silicones and silicones modified with alkyl groups. In the present patent application, "oils" is understood to mean compounds and/or mixtures of compounds which are insoluble in water, presenting a liquid appearance at a temperature of 25° C.

As examples of waxes that may be combined with the composition ($C_1$), mention may be made of beeswax, carnauba wax, candelilla wax, ouricury wax, Japan wax, cork fiber wax, sugarcane wax, paraffin waxes, lignite waxes, microcrystalline waxes, lanolin wax; ozokerite; polyethylene wax; silicone waxes; plant waxes; fatty alcohols and fatty acids that are solid at ambient temperature; glycerides that are solid at ambient temperature. In the present patent application, "waxes" is understood to mean compounds and/or mixtures of compounds which are insoluble in water, presenting a solid appearance at a temperature of greater than or equal to 45° C.

As examples of active principles which may be combined with the composition ($C_1$), mention may be made of vitamins and their derivatives, in particular their esters, such as retinol (vitamin A) and its esters (for example retinyl palmitate), ascorbic acid (vitamin C) and its esters, sugar derivatives of ascorbic acid (such as ascorbyl glucoside), tocopherol (vitamin E) and its esters (such as tocopheryl acetate), vitamin B3 or B10 (niacinamide and its derivatives); compounds showing a lightening or depigmenting action on the skin, such as ω-undecylenoyl phenylalanine sold under the name Sepiwhite™ MSH, Sepicalm™ VG, the glycerol monoester and/or the glycerol diester of ω-undecylenoyl phenylalanine, w-undecylenoyl dipeptides, arbutin, kojic acid, hydroquinone; compounds showing a soothing action, in particular Sepicalm™ S, allantoin and bisabolol; antiinflammatory agents; compounds showing a moisturizing action, such as urea, hydroxyureas, glycerol, polyglycerols, glycerol glucoside, diglycerol glucoside, polyglyceryl glucosides, xylityl glucoside; polyphenol-rich plant extracts, such as grape extracts, pine extracts, wine extracts or olive extracts; compounds showing a slimming or lipolytic action, such as caffeine or its derivatives, Adiposlim™ Adipoless™, fucoxanthin; N-acylated proteins; N-acylated peptides, such as Matrixyl™; N-acylated amino acids; partial hydrolyzates of N-acylated proteins; amino acids; peptides; total hydrolyzates of proteins; soybean extracts, for example Raffermine™; wheat extracts, for example Tensine™ or Gliadine™; plant extracts, such as tannin-rich plant extracts, isoflavone-rich plant extracts or terpene-rich plant extracts; extracts of freshwater or marine algae; marine plant extracts; marine extracts in general, such as corals; essential waxes; bacterial extracts; ceramides; phospholipids; compounds showing an antimicrobial action or a purifying action, such as Lipacide™ C8G, Lipacide™ UG, Sepicontrol™ A5; Octopirox™ or Sensiva™ SC50; compounds showing an energizing or stimulating property, such as Physiogenyl™, panthenol and its derivatives, such as Sepicap™ MP; anti-aging active principles, such as Sepilift™ DPHP, Lipacide™ PVB, Sepivinol™, Sepivital™, Manoliva™, Phyto-Age™, Timecode™; Survicode™; antiphotoaging active principles; active principles which protect the integrity of the dermoepidermal junction; active principles which increase the synthesis of the components of the extracellular matrix, such as collagen, elastins or glycosaminoglycans; active principles which act favorably on chemical cell communication, such as cytokines, or physical cell communication, such as integrins; active principles which create a feeling of "heating" on the skin, such as activators of cutaneous microcirculation (such as nicotinic acid derivatives) or products which create a feeling of "coolness" on the skin (such as menthol and derivatives); active principles which improve cutaneous microcirculation, for example venotonics; draining active principles; active principles having a decongestant purpose, such as *Ginkgo biloba*, ivy, horse chestnut, bamboo, ruscus, butcher's broom, *Centella asiatica*, fucus, rosemary or willow extracts; agents for tanning or browning the skin, for example dihydroxyacetone (DHA), erythruiose, mesotartaric aldehyde, glutaraidehyde, glyceraldehyde, alioxan or ninhydrin, plant extracts, for example extracts of red woods of the genus *Pterocarpus* and of the genus *Baphia*, such as *Pteropcarpus santalinus, Pterocarpus osun, Pterocarpus soyauxii, Pterocarpus erinaceus, Pterocarpus indicus* or *Baphia nitida*, such as those described in the European patent application EP 0 971683; agents known for their action in facilitating and/or accelerating tanning and/or browning of human skin, and/or for their action in coloring human skin, for example carotenoids (and more particularly β-carotene and γ-carotene), the product sold under the brand name "Carrot Oil" (INCI name: *Daucus carota, Helianthus annuus* sunflower oil) by the company Provital, which contains carotenoids, vitamin E and vitamin K; tyrosine and/or its derivatives, known for their effect on the acceleration of the tanning of human skin in combination with exposure to ultraviolet radiation, for example the product sold under the brand name "SunTan Accelerator™" by the company Provital, which contains tyrosine and riboflavins (vitamin B), the tyrosine and tyrosinase complex sold under the brand name "Zymo Tan Complex" by the company Zymo Line, the product sold under the band name Melano-Bronze™ (INCI name: acetyl tyrosine, monk's pepper extract (*Vitex agnus-castus*)) by the company Mibelle, which contains acetyl tyrosine, the product sold under the brand name Unipertan VEG-24/242/2002 (INCI name: butylene glycol and acetyl tyrosine and hydrolyzed vegetable protein and adenosine triphosphate) by the company Unipex, the product sold under the brand name "Try-Excell™" (INCI name: oleoyl tyrosine and *Luffa cylindrica* (seed) oil and oleic acid) by the company Sederma, which contains extracts of marrow seeds (or loofah oil), the product sold under the brand name "Actibronze™" (INCI name: hydrolyzed wheat protein and acetyl tyrosine and copper gluconate) by the company Alban Muller, the product sold under the brand name Tyrostan™ (INCI name: potassium caproyl tyrosine) by the company Synerga, the product sold under the brand name Tyrosinol (INCI name: sorbitan isostearate, glyceryl oleate, caproyl tyrosine) by the company Synerga, the product sold under the brand name Insta-Bronze™ (INCI name: dihydroxyacetone and acetyl tyrosine and copper gluconate) sold by the company Alban Muller, the product sold under the brand name Tyrosilane (INCI name: methylsilanol and acetyl tyrosine) by the company Exymol; peptides known for their melanogenesis-activating effect, for example the product sold under the brand name Bronzing SF Peptide powder (INCI name: dextran and octapeptide-5) by the company Infinitec Activos, the product sold under the trade name Melitane (INCI name: glycerin and aqua and dextran and acetyl hexapeptide-1) comprising acetyl hexapeptide-1 known for its α-MSH agonist action, the product sold under the brand name Melatimes Solutions™ (INCI name: butylene glycol, palmitoyl tripeptide-40) by the company Lipotec, sugars and sugar derivatives, for example the product sold under the brand name Tanositol™ (INCI name: inositol) by the company Provital, the product sold under the brand name Thalitan™ (or Phycosaccharide™ AG) by the company Codif International (INCI name: aqua and hydrolyzed algin (*Laminara digitata*) and magnesium sulfate and manganese sulfate) containing an oligosaccharide of marine origin (guluronic acid and mannuronic acid chelated with magnesium and manganese ions), the product sold under the brand name Melactiva™ (INCI name: maltodextrin, *Mucuna pruriens* seed extract) by the company Alban Muller, flavonoidrich compounds, for example the product sold under the brand name "Biotanning" (INCI name: hydrolyzed citrus *Aurantium dulcis* fruit extract) by the company Silab and known to be rich in lemon flavonoids (of the hesperidin type); agents intended for the treatment of head hair and/or body hair, for example agents which protect the melanocyes of the hair follicle, which are intended to protect said melanocytes against cytotoxic agents responsible for the senescence and/or the apoptosis of said melanocytes, such as mimetics of the activity of DOPAchrome tautomerase chosen from those described in the European patent application published under the number EP1515688 A2, synthetic molecules which mimic SOD, for example manganese complexes, antioxidant compounds, for example cyclodextrin derivatives, silica-containing compounds derived from ascorbic acid, lysine pyrrolidonecarboxylate or arginine pyrrolidonecarboxylate, combinations of mono- and diester of cinnamic acid and of vitamin C, and more generally those mentioned in the European patent application published under the number EP 1 515 688 A2.

As examples of antioxidants that may be combined with the composition ($C_1$), mention may be made of EDTA and salts thereof, citric acid, tartaric acid, oxalic acid, BHA (butylhydroxyanisole), BHT (butylhydroxytoluene), tocopherol derivatives such as tocopheryl acetate, mixtures of antioxidant compounds such as Dissolvine GL 47S sold by the company Akzo Nobel under the INCI name: tetrasodium glutamate diacetate.

As examples of sunscreens that may be combined with the composition ($C_1$), mention may be made of all those featuring in the modified Cosmetics Directive 76/768/EEC, Annex VII.

The organic sunscreens that may be combined with the composition ($C_2$) for topical use that is a subject of the present invention as defined above include the family of the benzoic acid derivatives, such as para-aminobenzoic acids (PABA), in particular monoglycerol esters of PABA, ethyl esters of N,N25 propoxy PABA, ethyl esters of N,N-diethoxy PABA, ethyl esters of N,N-dimethyl PABA, methyl esters of N,N-dimethyl PABA or butyl esters of N,N-dimethyl PABA; the family of the anthranilic acid derivatives, such as homomenthyl N-acetylanthranilate; the family of the salicylic acid derivatives, such as amyl salicylate, homomenthyl salicylate, ethylhexyl salicylate, phenyl salicylate, benzyl salicylate or p-isopropylphenyl salicylate; the family of the cinnamic acid derivatives, such as ethylhexyl cinnamate, ethyl 4-isopropylcinnamate, methyl 2,5-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate or mono(2-ethylhexanoyl)glyceryl di(para-methoxycinnamate); the family of the benzophenone derivatives, such as 2,4-dihydroxybenzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl 4'-phenylbenzophenone-2,5-carboxylate, 2-hydroxy-4-(n-octyloxy)benzophenone, 4-hydroxy-3-carboxybenzophenone; 3-(4'-methylbenzylidene)-d,l-camphor, 3-benzylidene-d,l-camphor, camphor benzalkonium methosulfate; urocanic acid, ethyl urocanate; the family of the sulfonic acid derivatives, such as 2-phenylbenzimidazole-5-sulfonic acid and its salts; the family of the triazine derivatives, such as hydroxyphenyl triazine, ethylhexyoxyhydroxyphenyl-4-methoxyphenyltazine, 2,4,6-trianilino(p-carbo-2'-ethylhexyl-1'-oxy)-1,3,5-triazine, the 4,4-((6-(((1,1-dimethylethyl)amino)carbonyl)phenyl)amino)-1,3,5-triazine-2,4-diyl diimino) bis-(2-ethylhexyl) ester of benzoic acid, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methyphenyl)benzotriazole; dibenzazine; dianisoylmethane, 4-methoxy-4"-t-butybenzoylmethane; 5-(3,3-dimethyl-2-norbornylidene)-3-pentan-2-one; the family of the diphenylacrylate derivatives, such as 2-ethylhexyl 2-cyano-3,3-diphenyl-2-propenoate or ethyl 2-cyano-3,3-diphenyl-2-propenoate; or the family of the polysiloxanes, such as benzylidene siloxane malonate.

Among the inorganic sunscreens, also called "mineral sunblocks", that may be combined with the composition ($C_2$) for topical use that is a subject of the present invention as defined above, mention may be made of titanium oxides, zinc oxides, cerium oxide, zirconium oxide, yellow, red or black iron oxides, and chromium oxides. These mineral sunblocks may or may not be micronized, may or may not have undergone surface treatments and may optionally be present in the form of aqueous or oily predispersions.

A further subject of the invention is a composition ($C_1$) as defined above for use thereof in a method of therapeutic treatment aiming to reduce and/or eliminate instances of prickling and/or tingling and/or itching and/or hotness and/or redness and/or cutaneous discomfort and/or tightness of the skin that are caused by inflammation of the human skin and/or the scalp. Preferably, the instances of prickling and/or tingling and/or itching and/or hotness and/or redness and/or cutaneous discomfort and/or tightness accompany skin pathologies such as urticaria, eczematous dermatitis, rosacea, psoriasis, herpes, photodermatosis, atopic dermatitis, contact dermatitis, lichen, prurigo, pruriginous diseases, fibrosis, disorders of collagen maturation, scleroderma, eczema.

BIBLIOGRAPHY (1): Chan et al., "A review of the pharmacological effects of *Arctium lappa*", Inflammopharmacol, 2011, 19:245-254).

(2): Pirvu et al., "Comparative studies on analytical, antioxidant, and antimicrobial activities of a series of vegetal extracts prepared from eight plant species growing in Romania", J planar Chromato 2014.

The examples that follow illustrate the invention without, however, limiting it.

DESCRIPTION OF THE PREFERRED EMBODIMENTS

A) Preparation Example $A_1$) Example for Preparing a Composition ($C_{1A}$) According to the Invention.

The burdock or *Arctium lappa* plants were obtained beforehand by germination of seeds for a period of 60 days under standard conditions, so as to reach a size of about 10 to 15 centimeters, after which they are transplanted to be placed under "soilless" cultivating conditions or in an aeroponic environment.

The roots of the burdock plants are thus soaked in a nutrient solution that is characterized by an electroconductivity of between 1.0 and 1.2 millisiemens and by a mass N/P/K (nitrogen/phosphorous/potassium) ratio, provided by the fertilizer, of about 15/10/30. This aeroponic cultivating phase is conducted for six weeks at a temperature regulated to 20° C., and makes it possible to obtain a root yield of 754 grams per square meter.

The fresh roots of the biomass thus obtained are removed and immersed for 15 minutes in a bath comprising a mixture comprising, per 100% of its mass, 70% by mass of 1,2-propanediol and 30% by mass of distilled water, at a temperature of 25° C.; the pH value of the distilled water was regulated beforehand to 2.0±0.2 by addition of a 75% by mass solution of phosphoric acid. The ratio of root biomass thus immersed for a volume of above-described mixture of 1,2-propanediol and water amounts to 1.0 kg of root biomass per 1 liter of mixture of 1,2-propanediol and water.

At the end of the immersion, the plants are removed from their exudation bath ($L_1$), which is retained, and the roots are drained and then cut, after which the remaining biomass is left to macerate for a period of 48 hours in a bath comprising a mixture comprising, per 100% of its mass, 70% by mass of 1,2-propanediol and 30% by mass of distilled water, at a temperature of 25° C.; the pH value of the distilled water was regulated beforehand to 2.0±0.2 by addition of a 75% by mass solution of phosphoric acid. The ratio of root biomass thus immersed for a volume of above-described mixture of 1,2-propanediol and water amounts to 0.5 kg of biomass per 1 liter of mixture of 1,2-propanediol and water.

At the end of this maceration phase, the biomass is separated from the maceration liquid ($L_2$), and said liquid ($L_2$) is subsequently filtered with a 50 micrometer bag filter.

The liquids ($L_1$) and ($L_2$) are subsequently combined, and a required amount of 1,2-propanediol is added in order to adjust the content by mass thereof to 70%, to give the liquid ($L_3$), which is subsequently filtered through a 1 micrometer membrane in order to clarify it, and lastly by sterilizing filtration with a 0.2 micrometer membrane, to produce the composition ($C_{1A}$).

$A_2$) Example for Preparing a Comparative Composition ($C_{comp}$).

The seedlings obtained from the same batch of seeds as those used for obtaining the seedlings subsequently cultivated aeroponically (example $A_1$) are used for earth cultivation of said seedlings for a period of six weeks.

At the end of this period, the plants are transplanted, the fresh roots are cleaned, cut and ground, and then said ground material obtained is extracted by a conventional liquid-solid extraction process (maceration, stirring, filtration) using a 70/30 1,2-propanediol/distilled water solvent mixture, at a temperature of 25° C., with a mass fresh roots/solvent medium ratio of 0.5 kg of biomass per 1 liter of mixture of 1,2-propanediol and water; the pH value of the distilled water was regulated beforehand to 2.0±0.2 by addition of a 75% by mass solution of phosphoric acid.

At the end of this extraction phase, the biomass is separated from the liquid, which is then filtered using a 50 micrometer bag filter, then with a 1 micrometer membrane in order to clarify it, and lastly by sterilizing filtration with a 0.2 micrometer membrane, to produce the composition ($C_{comp}$).

$A_3$) Analytical Characterization of the Inventive Composition ($C_{1A}$) and the Comparative composition ($C_{comp}$).

The inventive composition ($C_{1A}$) and the comparative composition ($C_{comp}$) were characterized by analysis and the characteristics are given in table 7 below.

TABLE 7

| Analytical characteristics | Analytical method | Inventive composition ($C_{1A}$) | Comparative composition ($C_{comp}$) |
|---|---|---|---|
| Appearance | Visual | Yellow liquid | Yellow liquid |
| 1,2-Propanediol content | Gas chromatography (headspace) | 71.4% | 70.0% |
| pH | NFT 73-206 | 3.1 | 3.2 |
| Dry extract due to the plant in % by mass | Oven 105° C., 12 hours | 0.21% | 1.12% |
| Water in % by mass | (Standard NFT 73201) | 28.39% | 28.88% |
| Total amount of compounds of formula (Ia), of formula (Ib), of formula ($I_{C1}$) and of formula ($I_{C2}$), expressed in milligrams/gram of dry extract due to the plant | UHPLC-MS Instrument: Shimadzu Nexera X2 Column: Waters Xterra RP C18; 250 × 4.6 mm Mobile phase (with gradient): A) Water + formic acid B) Acetonitrile UV detector (330 nm) | 613.3 mg/g | 169.5 mg/g |

B) Demonstration of the Active Properties of Inventive Composition ($C_{1A}$) and Comparative Composition ($C_{comp}$).

$B_1$) Demonstration of the Prevention of Change in the Barrier Function of the Skin, on Reconstructed Human Epidermises.

B1.1. Principle of the Method

The *Staphylococcus epidermidis* and *Staphylococcus aureus* strains were cultured in BHI (Brain Heart Infusion) and NB (Nutrient Broth) media, respectively, at 37° C. for 24 hours. Reconstructed human epidermises with a surface area of 0.5 cm², cultured at 37° C. and under 5% $CO_2$, were colonized first with the *Staphylococcus epidermidis* strain for a period of 6 hours and then were colonized with the *Staphylococcus aureus* strain for 24 hours.

The inventive composition ($C_{1A}$) (1% v/v) was added to the reconstructed human epidermises at the same time as the *Staphylococcus epidermidis* strain, and then again with the *Staphylococcus aureus* strain.

The barrier function of the reconstructed human epidermises thus treated was evaluated:
  by measuring the trans-epithelial electrical resistance (TEER) of the reconstructed human epidermises, and
  by histological evaluation of said reconstructed human epidermises, and more particularly by hematoxylin and eosin staining, and by a "score" for said staining.

In the context of the histological evaluation, the effects on the barrier function of the reconstructed human epidermises were evaluated by a histological score on hematoxylin and eosin staining, which was awarded as follows:
  0=standard: no significant modification of the reference morphology 1=slight: significant modification of the *Stratum corneum*

2=moderate: significant modifications of the *Stratum corneum* and of the granular layer, reduction in keratohyalin and some necrotic cells 3=high: significant modifications of the basal layer with necrotic cells and intercellular holes and edemas 4=severe: loss of intercellular connection, detachment from the fabric of the polycarbonate filter, necrotic cells, absence of specific labelling.

A product is judged to protect the barrier function of the human epidermis if the histological score is rated "standard" (score 0) or "slight" (score 1).

[Reconstructed human epidermis colonized with *Staphylococcus* epidermidis+*Staphylococcus aureus* without addition of composition ($C_{LA}$)])

The results were analyzed statistically using a two-sided Student test and a significance threshold set at 5%, by pairwise comparison of the colonizations and treatments carried out. A difference between the efficacy of two products is considered to be:

significant if p<0.05;

"at the limit of significance" if 0.05≤p<0.1;

and not significant if p>0.1.

TABLE 8

|  | Measurement of the trans-epithelial electrical resistance of the surface of the reconstructed human epidermis Before colonization with the bacteria and/or treatment with composition ($C_{LA}$) (in ohm · cm$^2$) | Measurement of the trans-epithelial electrical resistance of the surface of the reconstructed human epidermis After colonization with the bacteria and/or treatment with composition ($C_{LA}$) (in ohm · cm$^2$) | Difference in the measurement of the trans-epithelial electrical resistance of the surface of the reconstructed human epidermis after colonization/treatment and before colonization/treatment (Δ1) (in ohm · cm$^2$) |
|---|---|---|---|
| Untreated reconstructed human epidermis (control) | 8073.33 +/− 1913.60 | 6900.00 +/− 1489.80 | −1173.33 |
| Reconstructed human epidermis colonized with *Staphylococcus epidermidis* + *Staphylococcus aureus* without addition of composition ($C_{LA}$) | 8094.44 +/− 1486.73 | 4726.11 +/− 2067.16 | −3368.33 (% versus control = +187%; p = 0.009) |
| Reconstructed human epidermis colonized with *Staphylococcus epidermidis* + *Staphylococcus aureus* and treated with composition ($C_{LA}$) 1% (v/v) (0.0136% of dry extract of composition ($C_{LA}$)) | 7647.22 +/− 1566.61 | 5645.56 +/− 911.52 | −2001.66 (% versus control = +71%; not significant) Percentage protection = 62% |

The equilibrium of the microbiota of the reconstructed human epidermis, with or without application of the composition ($C_{LA}$), was evaluated by studying the formation of colony and biofilm ultrastructures by SEM.

B.1.2. Results

B.1.2.1 Results Obtained Regarding the Protection of the Barrier Function of Reconstructed Human Epidermises by Measurement of Trans-Epithelial Electrical Resistance (TEER).

The TEER measurements performed on the reconstructed human epidermises, as a function of the associated treatments, are set out in table 8. A decrease in the trans-epithelial electrical resistance (TEER) demonstrates a degradation of the barrier function of the epidermis and, consequently, constitutes one of the factors in dehydration of the skin and in unesthetic effects which this dehydration may cause. A calculation is also made of the difference in the measurement of the trans-epithelial electrical resistance of the surface of the reconstructed human epidermis after colonization and before colonization (Δ1)

A calculation is also made of the percentage protection, according to the following formula:

% protection=Δ1 [Reconstructed human epidermis colonized with *Staphylococcus* epidermis+*Staphylococcus aureus* and treated with composition ($C_{LA}$) 1% (v/v)]−Δ1 [Reconstructed human epidermis colonized with *Staphylococcus* epidermidis+*Staphylococcus aureus* without addition of composition ($C_{LA}$)])/(Δ [Untreated reconstructed human epidermis (control)]−Δ1

When the reconstructed human epidermises are colonized with *Staphylococcus epidermidis* and *Staphylococcus aureus*, the TEER difference measured before and after the start of said colonization is −3373.33 ohm·cm$^2$, and exhibits a significant increase of 187% relative to the uncolonized and untreated reconstructed human epidermises (−1173.33 ohm·cm$^2$).

When the reconstructed human epidermises are contacted with composition (CA) at the same time as they are colonized with *Staphylococcus epidermidis* and *Staphylococcus aureus*, the TEER difference measured before and after the start of said colonization is −2001.66 ohm·cm$^2$, which represents a non-significant increase of 71% relative to the uncolonized and untreated reconstructed human epidermises (−1173.33 ohm·cm$^2$) and a protection of 62% relative to the reconstructed human epidermises colonized with *Staphylococcus epidermidis* and *Staphylococcus aureus*.

The result is that the application to the skin of a composition comprising composition ($C_{LA}$) makes it possible to prevent the degradation of the barrier function of the epidermis of the skin, before the skin is subjected to the action of bacteria which are known to have degrading effects on the barrier function of said epidermis of the skin.

B.1.2.2 Results Obtained Regarding the Protection of the Barrier Function of Reconstructed Human Epidermises by Histological Evaluation of Said Reconstructed Human Epidermises, by Hematoxylin and Eosin Staining.

The hematoxylin and eosin staining of the epidermises was evaluated by the awarding of a "score" as described above, and the results are set out in table 9 below:

TABLE 9

| Histological score | |
|---|---|
| Untreated reconstructed human epidermis (control) | 0 No significant modification vs reference morphology |
| Human epidermis colonized with *Staphylococcus epidermidis* + *Staphylococcus aureus* without addition of composition ($C_{1A}$) | 2 Modification of the structure of the viable epidermis with more intercellular spaces and cell clusters. |
| Reconstructed human epidermis colonized with *Staphylococcus epidermidis* + *Staphylococcus aureus* and treated with composition ($C_{1A}$) 1% (v/v) (0.0136% of dry extract due to the plant of composition ($C_{1A}$)) | 1 Reduction in damage, especially at the basal level and in the stratum corneum, where a more compact lamellar structure is observed |

When the reconstructed human epidermises were colonized with *Staphylococcus epidermidis* and *Staphylococcus aureus*, the histological score was evaluated at a level of 2, demonstrating a modification of the structure of the viable epidermis with more intercellular spaces and cell clusters.

When the reconstructed human epidermises were contacted with composition ($C_{1A}$) at the same time as being colonized with *Staphylococcus epidermidis* and *Staphylococcus aureus*, the histological score was evaluated at a level of 1, demonstrating a reduction in damage, especially at the basal level and in the *Stratum corneum*, where a more compact lamellar structure is observed.

The result is that the application to the skin of a composition comprising composition ($C_{1A}$) makes it possible to prevent the degradation of tissue cohesion and consequently of the barrier function of the epidermis in the face of an invasion of the transitory flora.

Furthermore, in the context of this histological study, the profile of colonization with the two bacteria (*Staphylococcus epidermidis* and *Staphylococcus aureus*) was evaluated by scanning electron microscopy (SEM, Zeiss Sigma Electron Microscope).

When the reconstructed human epidermises were colonized with *Staphylococcus epidermidis* alone, the bacterium is present uniformly on the surface of the reconstructed human epidermis, forming large aggregates and developing a biofilm which is characterized by filamentous polysaccharide structures observed with a magnification of ×10000 of the electron microscope.

When the reconstructed human epidermises were colonized with *Staphylococcus epidermidis* and *Staphylococcus aureus*, the appearance of a number of spherical aggregates of *Staphylococcus aureus* is observed on the surface of the reconstructed human epidermis, whereas a film of *Staphylococcus epidermidis* remains visible on the surface of said epidermis.

Likewise observed is the presence of large aggregates of *Staphylococcus aureus*, with a magnification of ×10000 of the electron microscope, forming a three-dimensional structure, hence indicating an early stage of development of a biofilm on the surface of the epidermis.

After application to the skin of a composition comprising composition ($C_{1A}$), the spherical aggregates of *Staphylococcus aureus* are no longer present, thus signifying that the addition of composition ($C_{1A}$) makes it possible to prevent the adhesion of the bacteria to the surface of the epidermis and the formation of the biofilm of *Staphylococcus aureus*. The biofilm of *Staphylococcus epidermidis* is still observed on the surface of the epidermis.

These observations show that composition ($C_{1A}$) enables a reduction in the adhesion and hence in the formation of biofilms of opportunistic pathogenic bacteria, such as for example *Staphylococcus aureus*, without detriment to the presence of commensal bacteria such as *Staphylococcus epidermidis*.

B.1.3. Conclusions

The combination of the measurement of the trans-epithelial electrical resistance with the histological evaluation of reconstructed human epidermises, before colonization by a commensal bacterium of the cutaneous flora, then by a pathogenic bacterium, constitutes a model which allows the study of the change in the barrier function and the equilibrium of the microbiota of said epidermis, and the incidence of prior treatments with complex compositions or extracts or formulations.

The collective results and observations obtained in sections B.1.2.1 and B.1.2.2 show that the composition ($C_{1A}$) enables prevention of degradation of the barrier function of the epidermis in human skin and, consequently, prevention of the appearance of inflammation and redness, when the skin is colonized by a commensal bacterium of the cutaneous flora, then by a pathogenic bacterium.

B₂) Demonstration of the Prevention of the Effect of Inventive Compositions on Inflammation Induced in the Event of Imbalance in the Microbiota B.2.1. Principle of the Method The anti-inflammatory effect of compositions was evaluated on normal human keratinocytes under conditions imitating an imbalance in the cutaneous microbiota through the activation of 3 TLRs (Toll-Like Receptors). These receptors are activated by recognition of specific elements of the microbes, and their function is to alert the immune system in order to activate the body's defenses. In this model, the imbalance in the microbiota was modeled with various stimuli imitating a skin infection:

TLR-5 was activated by flagellin (the main protein of the flagellar filament, present in virtually all bacteria)

TLR-2 was activated by zymosan (glycoprotein complex extracted from yeast membranes)

TLR-3 was activated by poly(I:C) (a synthetic analog of the double-stranded RNA found in viruses)

The effect of the compositions tested was evaluated on the basis of their capacity to modulate the production of IL-8 and of hBD2 induced by these stimuli, using specific "ELISA" kits. The concentration of total proteins was also evaluated, in order to standardize the production of cytokin (IL-8) and of antimicrobial peptide (hBD2).

Statistical Elements:

The values are expressed as means+/−sem [standard error of the mean=standard deviation/root (number of values)].

For each treatment, a calculation was made of:

% protection=100×[mean (cells+treatment)−mean (stimulated cells)]/[mean (unstimulated cells)− mean (stimulated cells)]

The statistical analysis of the results was conducted using a two-sided Student test with a significance threshold set at 5%, by pairwise comparison of the series of values. A difference between the efficacy of two products is considered to be:

significant if $p<0.05$;

"at the limit of significance" if $0.05 \leq p < 0.1$;

and not significant if $p > 0.1$.

B.2.2. Results Obtained

In the three tables which follow: For stimulated cells: * p<0.001 vs unstimulated cells. For treated and stimulated cells: * p<0.001 vs stimulated cells.

The results obtained following activation of TLR-5 by flagellin, the results are set out in table 10 below:

TABLE 10

|  | IL-8 (pg/mg proteins) | hBD2 (pg/mg proteins) |
| --- | --- | --- |
| Control (unstimulated cells) | 22 +/− 1 | 39 +/− 5 |
| Cells stimulated with flagellin | 906 +/− 42*** | 629 +/− 65*** |
| Cells stimulated with flagellin + positive reference (IKK inhibitor × 10 μM) | 304 +/− 9 68%*** | 90 +/− 11 91%*** |
| Cells stimulated with flagellin + composition ($C_{1A}$) at 0.074% (v/v) | 363 +/− 29 61%*** | 126 +/− 7 85%*** |

The results obtained following activation of TLR-2 by zymosan, the results are set out in table 11 below:

TABLE 11

|  | IL-8 (pg/mg proteins) | hBD2 (pg/mg proteins) |
| --- | --- | --- |
| Control (unstimulated cells) | 21 +/− 1 | 53 +/− 9 |
| Cells stimulated with zymosan | 1421 +/− 31*** | 558 +/− 33*** |
| Cells stimulated with zymosan + positive reference (IKK inhibitor × 10 μM) | 373 +/− 8 75%*** | 55 +/− 9 100%*** |
| Cells stimulated cells with zymosan + composition ($C_{1A}$) at 0.074% | 661 +/− 28 54%*** | 267 +/− 8 58%*** |

The results obtained following activation of TLR-3 by poly(I:C), the results are set out in table 12 below:

TABLE 12

|  | IL-8 (pg/mg proteins) | hBD2 (pg/mg proteins) |
| --- | --- | --- |
| Control (unstimulated cells) | 22 +/− 2 | 40 +/− 45 |
| Cells stimulated with poly(I:C) | 15109 +/− 147*** | 480 +/− 26*** |
| Cells stimulated with poly(I:C) + positive reference (bafilomycin 100 nM) | <19 100%*** | 17 +/− 2 100%*** |
| Cells stimulated with poly(I:C) + composition ($C_{1A}$) at 0.074% | 3986 +/− 520 74%*** | 105 +/− 20 85%*** |
| Cells stimulated with poly(I:C) + composition ($C_{1A}$) 3.13 × $10^{-4}$% dry extract | 875 +/− 40 94%*** | 22 +/− 3 100%*** |

B.2.3. Analyses and Conclusions

When TLR-5 is activated by flagellin, and when the cells are treated with 0.074% of inventive composition ($C_{1A}$), an increase in the production of IL-8 is observed of 61% relative to the production of IL-8 when the cells are not treated. Similarly, when the cells are treated with inventive composition ($C_{1A}$), an increase in the production of hBD2 is observed of 85% relative to the production of hBD2 when the cells are not treated.

When TLR-2 is activated by zymosan, and when the cells are treated with 0.074% of inventive composition ($C_{1A}$), an increase in the production of IL-8 is observed of 54% relative to the production of IL-8 when the cells are not treated. Similarly, when the cells are treated with inventive composition ($C_{1A}$), an increase in the production of hBD2 is observed of 58% relative to the production of hBD2 when the cells are not treated.

When TLR-3 is activated by poly(I:C), and when the cells are treated with 0.074% of inventive composition ($C_{1A}$), an increase in the production of IL-8 is observed of 74% relative to the production of IL-8 when the cells are not treated. Similarly, when the cells are treated with inventive composition ($C_{1A}$), an increase in the production of hBD2 is observed of 85% relative to the production of hBD2 when the cells are not treated.

When TLR-2, TLR-3 and TLR-5 are activated, and especially by simulation of an infection (bacterium, yeast, virus), the combination of inventive composition ($C_{1A}$) enables a reduction in the overproduction of cytokine IL-8 and of antimicrobial peptide hBD2, thus showing its capacity to reduce the inflammation induced by the imbalance in the microbiota. Consequently, the combination of inventive composition ($C_{1A}$) enables a reduction in the overproduction of cytokine IL-8 and of antimicrobial peptide hBD2, acts on the limitation of the phenomenon of skin inflammation or scalp inflammation, and therefore enables a reduction in the unesthetic effects associated with acne.

$B_3$) Demonstration of the Effect of the Inventive Composition on Preventing Redness and Burning and/or Itching Sensations Following the Induction of Physical or Chemical Irritation, for Reactive Skin B.3.1. Principle of the Method The method involves evaluating the effect of the test compositions on the equilibrium of the microbiota and of the barrier function, able to contribute to soothing reactive skin activated by mechanical or chemical stresses.

A population was recruited of 20 women aged from 18 to 65 years, having sensitive skin (on the basis of their declaration and of a stinging test ≥4).

The "stinging test" is used to identify persons having particular skin reactivity on the face. It involves applying a chemical stress (five depositions of a 10% by mass lactic acid solution) to the nasolabial fold, comparatively to physiological saline applied simultaneously from the other side. The subject evaluates the sensations of burning and stinging after 15 seconds, then 30 seconds, 2 minutes and 5 minutes, following application, according to the following evaluation scale: 0=no sensation; 1=slight sensation; 2=moderate sensation; 3=intense sensation. For each subject, the sum of scores is calculated and, if it is greater than or equal to 4, the subject is qualified as a subject with reactive skin.

The population of 20 persons selected applied the formula containing the inventive composition (C1A) and the placebo formula to half the face, twice a day, for 14 days. After 14 days of application, the population of subjects underwent mechanical stress and chemical stress to evaluate the soothing effect of the test compositions:

The skin reactivity was first evaluated by measuring the red color of the skin, using a chromameter, which measures the parameter "a". The mechanical stress was then formed on the cheeks by five operations of "stripping" (stripping/peeling), which are carried out in succession and which remove the first surface layers of the skin. The products were then applied (one to each side of the face) and the skin reactivity was measured again by chromametry, by measuring the parameter "a" 30 minutes after the first measurement. The difference in the parameter "Δa" before and 30 minutes after was calculated as follows:

For each subject (i), $\Delta a_i$=value of parameter (a) 30 minutes after first measurement−value of parameter (a) before application.

For the collective population, $\Delta a_{mean}=(\Sigma \Delta a_i)$/number of subjects The chemical stress was performed by five applications of a 10% lactic acid solution to the nasolabial folds. Each subject (i) evaluated (using the same scale as before) the sensations of burning and stinging after 15 seconds following the application of the lactic acid (recorded as "$S_{i0}$"), and then the products were applied (one to each side of the face), and again each subject (i) evaluated the sensations of burning and stinging at 30 seconds (recorded as "$S_{i30s}$"), 2 minutes (recorded as "$S_{i2min}$"), and 5 minutes (recorded as "$S_{i5min}$").

For each subject (i), a calculation is made of $\Delta S_i=(S_{i30s}+S_{i2min}+S_{i5min})-S_{i0}$ For the collective population, the calculation is $\Delta S_{mean}=(\Sigma S_i)$/number of subjects B.3.2. Results Obtained Evaluation of the redness induced by mechanical stress ($\Delta a_{mean}$)

The parameters $\Delta a_{mean}$ measured are as follows:

$\Delta a_{mean}$=1.41 for the group for which the parameter "a" was measured on the half-faces to which the placebo formula was applied.

$\Delta a_{mean}$=0.57 for the group for which the parameter "a" was measured on the half-faces to which the formula containing composition (CA) was applied.

The application of the formula containing composition ($C_{1A}$) therefore allows a 60% limitation of the parameter $\Delta a_{mean}$, and therefore enables a limitation in the phenomenon of redness associated with skin inflammation induced by mechanical stress.

Evaluation of the sensations of burning and stinging induced by chemical stress ($\Delta S_{mean}$)

$\Delta S_{mean}$=1 for the group for which the criterion $\Delta S_{mean}$ was measured on the half-faces to which the placebo formula was applied.

$\Delta S_{mean}$=0.8 for the group for which the criterion $\Delta S_{mean}$ was measured on the half-faces to which the formula containing composition ($C_{1A}$) was applied.

The application of the formula containing composition ($C_{1A}$) therefore enables a reduction in the criterion of evaluation associated with chemical stress, $\Delta S$, of 20%, and hence enables a reduction in the phenomenon of the sensations of burning and stinging of the human skin induced by chemical stress.

B₄) Demonstration of the Effect of Composition ($C_{1A}$) on Inflammation Induced in the Event of Imbalance in the Microbiota (Anti-Lipase Activity)

B.4.1. Principle of the Method

The subject of the method is to study the capacity of a composition to provoke and regulate the activity of the lipase enzyme by an in tubo method, said enzyme having an inflammatory action.

Lipase has the capacity to convert the colorless 1,2-diglyceride into glycerol, which is pink in color.

The samples for the evaluation test are placed in tubo in the presence of lipase and of 1,2-diglyceride, and the absorbance of the samples is measured in a spectrophotometer at a wavelength of 570 nm at the end of their preparation, then after 60 minutes of incubation at 37° C. under the same spectral conditions. By virtue of a range of glycerol, the lipase activity of the samples can be calculated, as can the percentage inhibition, by the following formulas:

Lipase activity=(amount of glycerol formed between 0 and 60 minutes)/(60 minutes×sample volume)

Percentage inhibition=100×[(lipase activity of control group)−(lipase activity of test product)]/ (lipase activity of control group)

Statistical Elements:

The values are expressed as means+/−standard deviation.
The statistical analysis of the results was conducted using a two-sided Student test with a significance threshold set at 5%, by pairwise comparison of the series of values.
A difference between the efficacy of two products is considered to be:
  significant if p<0.05;
  "at the limit of significance" if 0.05≤p<0.1;
  and not significant if p>0.1.

B.4.2. Results Obtained

The results obtained are set out in table 13 below (*** p<0.001 vs control).

TABLE 13

| Products tested | Lipase activity (mU/mL) | % inhibition of the lipase |
|---|---|---|
| Control | 4.21 +/− 0.02 | 0 |
| Positive reference (Vitamin C) | 2.11 +/− 0.01 | 50*** |
| Composition ($C_{1A}$) at 1% by mass | 0.92 +/− 0.01 | 78*** |
| 70% propylene glycol at 1% | 6.40 +/− 0.05 | — |

B.4.3. Analysis of the Results

The measurements set out in table 13 show that the treatment with inventive composition ($C_{1A}$) very significantly reduces the activity of the lipase, since the percentage inhibition measured is 78%.

The inventive composition ($C_{1A}$) makes it possible to limit the activity of the lipase and therefore to reduce the unesthetic effects of skin inflammation linked to the activity of said lipase.

B) General Conclusions Regarding the Biological Evaluations Employing Inventive Composition ($C_{1A}$).

The experimental evaluations in this section have shown that inventive composition ($C_{1A}$) makes it possible to limit the formation of a biofilm of pathogenic bacteria (in the present case, *Staphylococcus aureus*), but without affecting its viability nor that of commensal bacteria (such as for example *Staphylococcus epidermidis*).

It has also been established that when TLR-2, TLR-3 and TLR-5 are activated, and especially by simulation of an infection (bacterium, yeast, virus), the combination of inventive composition ($C_{1A}$) enables a reduction in the overproduction of cytokine IL-8 and of antimicrobial peptide hBD2, thus showing its capacity to reduce the inflammation induced by the imbalance in the microbiota;

the application of the formula containing composition ($C_{1A}$) therefore makes it possible to reduce the phenomenon of redness associated with skin inflammation;

the application of the formula containing composition ($C_{1A}$) makes it possible to reduce the phenomenon of the sensations of burning and stinging of human skin.

The result is that inventive composition ($C_{1A}$) can be used with the goal of preventing or slowing the appearance of the unesthetic signs associated with inflammation of the skin and/or scalp.

C) Formulations

In the following formulas, the percentages are expressed by weight of the formulation.

C.1 Face Makeup Remover Fluid

| Formula | |
|---|---|
| Composition ($C_{1A}$) | 10.00% |
| Methyl paraben | 0.15% |
| Phenoxyethanol | 0.80% |
| Sepicalm ™ S | 1.00% |
| Perfume/Fragrance | 0.10% |
| Water | qs 100.00% |

Procedure: Mix the various ingredients in the water with magnetic stirring, in the order indicated, and adjust the pH to about 7.

C.2 Infant Hair and Body Shampoo

| | Formula | |
|---|---|---|
| A | Composition ($C_{1A}$) | 15.00% |
| | Proteol ™ APL | 5.00% |
| | Sepicide ™ HB | 0.50% |
| | Perfume/Fragrance | 0.10% |
| B | Water | 20.00% |
| | Capigel ™ 98 | 3.50% |
| C | Water | qs 100.00% |
| | Sepicide ™ Cl | 0.30% |
| | Colorant | qs |
| | Sodium hydroxide | qs pH = 7.2 |

Procedure: Mix composition ($E_4$) with the Proteol™ APL and the Sepicide™ HB (Phase A). Dilute the Capigel™ 98 in a portion of the water and add it to phase A obtained previously (Phase B). Add the rest of the water to phase B, followed by the Sepicide™ CI and the colorant. Adjust the pH of the mixture to about 7.2 with sodium hydroxide.

C.3 Eye Makeup Remover Wipes

| | Formula | |
|---|---|---|
| A | Composition ($C_{1A}$) | 3.00% |
| B | Sepicide ™ HB2 | 0.50% |
| C | Sepicalm ™ VG | 0.50% |
| | Perfume/Fragrance | 0.05% |
| D | Water | qs 100.00% |

Procedure: Mix the ingredients of phase B and those of phase C in phase A until the solution is clear. Add phase D.

C.4 Mid Foaming Gel

| | Formula | |
|---|---|---|
| A | Composition ($C_{1A}$) | 8.50% |
| | Proteol ™ APL | 3.00% |
| | EUXYL ™ PE9010 | 1.00% |
| | Perfume/Fragrance | 0.10% |
| B | Water | qs 100.00% |
| | Lactic acid | qs pH = 6.0 |

Procedure: Dissolve the perfume and the preserving agent Euxyl™ PE9010 in the mixture composed of composition $E_4$ and the Proteol™ APL (phase A). Add the water and adjust the pH to about 6.0 with lactic acid.

C.5 Frequent-Use Shampoo

| | Formula | |
|---|---|---|
| A | Composition ($C_{1A}$) | 12.80% |
| | Proteol ™ OAT | 5.00% |
| | Euxyl ™ PE9010 | 1.00% |
| | Perfume/Fragrance | 0.30% |
| | Water qs | 100.00% |
| B | Montaline ™ C40 | 8.50% |
| | Lactic acid | qs pH = 6.0 |

Procedure: Mix all the ingredients of phase A and, after homogenization, add the Montaline™ C40 and adjust the pH to about 6.0 with lactic acid.

C.6 Ultra-Mild Baby Shampoo

| | Formula | |
|---|---|---|
| A | Composition ($C_{1A}$) | 10.00% |
| | Amisoft ™ CS-11 | 4.00% |
| | Perfume/Fragrance | 0.10% |
| | Sepicide ™ HB | 0.30% |
| | Sepicide ™ Cl | 0.20% |
| | Water | qs 100.00% |
| B | Water | 20.00% |
| | Capigel ™ 98 | 3.50% |
| | Trometamine | qs pH = 7.2 |

Procedure: Mix all the ingredients of phase A, in the order indicated, until a clear phase A is obtained. Separately, add the Capigel™ 98 to the water and then add this phase B thus prepared to phase A and adjust the pH to 7.2 using tromethamine.

C.7 Baby Cleansing Milk

| | Formula | |
|---|---|---|
| A | Simulsol ™ 165 | 2.00% |
| | Montanov ™ 202 | 1.00% |
| | Lanol ™ 99 | 3.00% |
| | Dimethicone | 1.00% |
| | Isohexadecane | 3.00% |
| B | Water | qs 100.00% |
| C | Sepiplus ™ 400 | 0.30% |
| D | Composition ($C_{1A}$) | 6.35% |
| E | Sepicide ™ HB | 0.30% |
| | DMDM Hydantoin | 0.20% |
| | Perfume/Fragrance | 0.10% |

Procedure: Heat, separately, phases A and B constituted by mixing the various constituents. Add phase C to the hot fatty phase and make the emulsion by pouring in the aqueous phase; homogenize for a few minutes with vigorous stirring (by means of a rotor/stator turbomixer). Next, add phase D to the hot emulsion and cool the emulsion with moderate stirring down to room temperature. Add phase E at 40° C.

C.8 Cleansing Powder Lotion for Sensitive Skin

| | Formula | |
|---|---|---|
| A | Lipacide ™ C8G | 0.95% |
| | Methyl paraben | 0.10% |
| | Ethyl paraben | 0.024% |
| | Propyl paraben | 0.0119% |
| | Butyl paraben | 0.024% |
| | Isobutyl paraben | 0.0119% |
| | Water | 20.00% |
| | Disodium EDTA | 0.10% |
| | Triethanolamine | 1.38% |
| B | Composition ($C_{1A}$) | 1.80% |
| | Perfume/Fragrance | 0.10% |
| C | Sepicalm ™ S | 0.28% |
| | Water | qs 100.00% |
| | Lactic acid | qs pH = 5.2 |
| D | Micropearl ™ M310 | 5.00% |

Procedure: Dissolve the ingredients of phase A in the water at 80° C. Separately, dissolve the perfume in composition ($E_4$) to prepare phase B. Add the cooled phase A to phase B, then introduce the Sepicalm™ S and the remaining water. Check the final pH and adjust to about 5.2 if necessary. Next, add the Micropearl™ M310.

C.9 Infant Shower Gel

| | Formula | |
|---|---|---|
| A | Water | 56.06% |
| | Sepimax ™ Zen | 3.00% |
| | Sepiplus ™ S | 0.80% |
| B | Proteol ™ OAT | 20.80% |
| | Oramix ™ NS 10 | 9.30% |
| | Amonyl ™ 265 BA | 5.10% |
| C | Composition ($C_{1A}$) | 2.00% |
| | Glyceryl glucoside | 1.00% |
| | Phenoxyethanol & ethylhexylglycerin | 1.00% |
| | Perfume/Fragrance | 0.90% |
| | Colorant | 0.04% |

Procedure: Disperse the Sepimax™ ZEN in the water and stir using a mechanical stirrer equipped with a deflocculator, a counter-rotating propeller and an anchor paddle, until a perfectly smooth gel is obtained. Add the Sepiplus™ S and then stir until the mixture is homogeneous. Next, add the ingredients of phase B, homogenize and individually add the additives of phase C. Adjust the pH to 6.0-6.5.

C.10 BB Cream

| | Formula | |
|---|---|---|
| A | Easynov ™ | 2.30% |
| | Lanol ™ 99 | 1.00% |
| | Sepimat ™ H10W | 1.00% |
| | Ethylhexyl methoxycinnamate | 5.00% |
| B | Cyclomethicone | 6.00% |
| | Triethoxycaprylsilane & alumina-silane & titanium oxide | 8.00% |
| | Red iron oxide & triethoxycaprylsilane | 0.24% |
| | Yellow iron oxide & triethoxycaprylsilane | 0.66% |
| | Black iron oxide & triethoxycaprylsilane | 0.09% |

| | Formula | |
|---|---|---|
| | Perfume/Fragrance | 0.10% |
| C | Water | qs 100% |
| | Sepinov ™ EMT10 | 1.20% |
| D | Composition ($C_{1A}$) | 2.00% |
| | Sepitonic ™ M3 | 1.00% |
| | Phenoxyethanol & ethylhexylglycerin | 1.00% |

Procedure: Prepare phase B by mixing the various ingredients and homogenize using a mixer equipped with a rotor-stator system at a spin speed of 4500 rpm, for a time of 6 minutes. Prepare phase C by adding the Sepinov™ EMT10 to the mixture of water and glycerol, and homogenize using a mixer equipped with a rotor-stator system at a spin speed of 4000 rpm for 4 minutes. Add phases A and B to phase C, and stir the resulting mixture using a mechanical stirrer equipped with an anchor paddle, at a speed of 30 rpm for 2 minutes, and then at a speed of 50 rpm for 20 minutes. Add the components of phase 5 one by one and stir at a speed of 50 rpm for 25 minutes.

C.11 High-Protection Sun Spray with an SPF of Greater than 30

| | Formula | |
|---|---|---|
| A | Montanov ™L | 1.00% |
| | Montanov ™ 82 | 1.00% |
| | C12-15 Alkyl benzoate | 17.00% |
| | Dimethicone | 3.00% |
| | Octocrylene | 6.00% |
| | Ethylhexyl methoxycinnamate | 6.00% |
| | Bis(ethylhexyloxyphenol)methoxy-phenyltriazine | 3.00% |
| | Tocopherol | 0.05% |
| B | Water | qs 100% |
| C | Simulgel ™ INS 100 | 0.50% |
| | Cyclodimethicone | 5.00% |
| D | Composition ($C_{1A}$) | 3.00% |
| | Phenoxyethanol & ethylhexylglycerin | 1.00% |
| | Perfume/Fragrance | 0.20% |
| E | Methylenebis(benzotriazolyl) Tetramethylbutylphenol | 10.00% |
| | 25% Citric acid | qs pH = 5 |

Sepicalm™ S: Mixture of N-cocoyl amino acids, sarcosine, potassium aspartate and magnesium aspartate as described in WO 98/09611;

Proteol™ APL: Mixture of sodium salts of N-cocoyl amino acids, obtained by acylation of amino acids characteristic of apple juice;

Sepicide™ HB: Mixture of phenoxyethanol, methyl paraben, ethyl paraben, propyl paraben and butyl paraben, which is a preserving agent;

Capigel™ 98: Acrylate copolymer;

Sepicide™ CI: Imidazoline urea, which is a preserving agent;

Sepicide™ HB: Mixture of phenoxyethanol, methyl paraben, ethyl paraben, propyl paraben, butyl paraben and isobutyl paraben, which is a preserving agent;

Sepicalm™ VG: Mixture of N-palmitoyl proline in sodium salt form and of extract of *Nymphea alba* blossom;

Euxyl™ PE9010: Mixture of phenoxyethanol and ethylhexylglycerin;

Proteol™ OAT: Mixture of N-lauryl amino acids obtained by total hydrolysis of oat protein as described in WO 94/26694;

Montaline™ C40: Chloride salt of monoethanolamine cocamidopropyl betainamide;

Amisoft™ CS-11: Sodium salt of N-cocoyl glutamate;

Simulsol™ 165: Mixture of PEG-100 stearate and glyceryl stearate;

Montanov™ 202 (arachidyl alcohol, behenyl alcohol and arachidyl glucoside) is a self-emulsifying composition such as those described in EP 0 977 626;

Lanol™99: Isononyl isononanoate;

Sepiplus™ 400: Self-invertible inverse latex of polyacrylates in polyisobutene and including polysorbate 20, as described in WO2005/040230;

Lipacide™ C8G: Capryloylglycine sold by the company SEPPIC;

Micropearl™ M310: Crosslinked polymethyl methacrylate polymer in powder form, used as a texture modifier;

Sepimax™ Zen (INCI name: Polyacrylate Crosspolymer-6): Thickening polymer in the form of a powder;

Sepiplus™ S (INCI name: Hydroxyethyl Acrylate/Sodium Acryloyldimethyl Taurate Copolymer & Polyisobutene & PEG-7 Trimethylolpropane Coconut Ether): Self-invertible inverse latex;

Amonyl™ 265 BA (INCI name: Cocoyl betaine): Foaming amphoteric surfactant;

Sepinov™ EMT10 (INCI name: Hydroxyethyl Acrylate/Sodium Acryloyldimethyl Taurate Copolymer): Thickening copolymer in the form of a powder;

Easynov™ (INCI name: Octyldodecanol and Octyldodecyl Xyloside and PEG-30 Dipolyhydroxystearate): Emulsifying agent of lipophilic tendency;

Sepimat™ H10 FW (INCI name: Methyl Methacrylate Crosspolymer and Squalane): Polymer used as texturing agent;

Sepitonic™ M3 (INCI name: Magnesium Aspartate and Zinc Gluconate and Copper Gluconate): Mixture used as free-radical scavenger and energizing agent for cells;

Montanov™ L (INCI name: C14-22 Alcohols and C12-20 Alkylglucoside): Emulsifying agent;

Montanov™ 82 (INCI name: Cetearyl Alcohol and Cocoglucoside): Emulsifying agent;

Simulgel™ INS100 (INCI name: Hydroxyethyl Acrylate/Sodium Acryloyldimethyl Taurate Copolymer and isohexadecane and Polysorbate 60): Polymeric thickener.

The invention claimed is:

1. A method of therapeutic treatment of inflammation of the human skin and/or the scalp, the method comprising:
   I. providing a cosmetic composition ($C_1$) comprising per 100% of mass:
   a) from 60.0% by mass to 75.0% by mass of an organic solvent ($SO_1$) selected from the group consisting of 1,2-propanediol, 1,3-propanediol, 1,4-butanediol, 1,3-butanediol, 1,2-butanediol, 2-methyl-2,4-pentanediol, 1,6-hexanediol, 1,8-octanediol, and mixtures thereof;
   b) from 0.1% by mass to 2.0% by mass of a composition (ES), wherein said composition (ES) comprises per 100% of mass:
   greater than or equal to 200 mg/g of:
      at least one compound of formula (Ia) corresponding to formula (I):

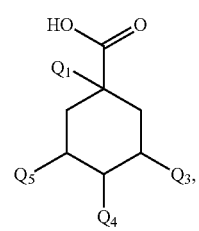

for which $Q_1$ represents the maloyl radical of formula (IIIa) or of formula (IIIb):

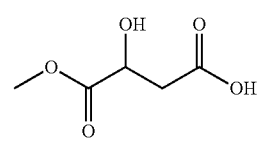

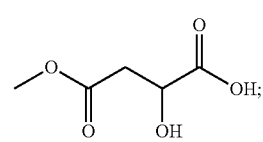

and $Q_3$ and $Q_4$ and $Q_5$, which are identical, each represent the caffeoyl radical of formula (II):

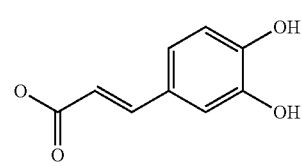

at least one compound of formula (Ib) corresponding to formula (I) for which $Q_1$ represents the caffeoylmaloyl radical of formula (IVa) or of formula (IVb):

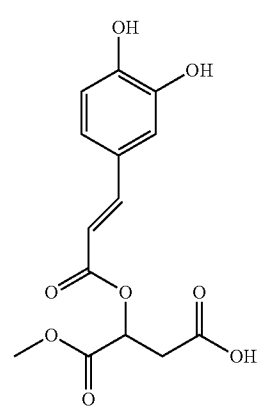

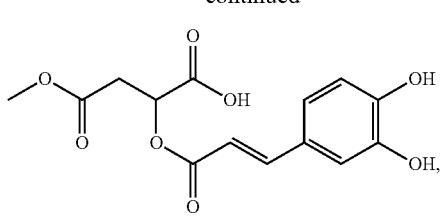

(IVb)

$Q_3$ and $Q_5$ each represent the caffeoyl radical of formula (II) and $Q_4$ represents the hydroxyl radical, and at least one compound of formula (Ic) selected from:
the compound of formula ($Ic_1$) corresponding to formula (I) for which $Q_1$ and $Q_5$ each represent the caffeoyl radical of formula (II), $Q_3$ represents the hydroxyl radical and $Q_4$ represents the caffeoyl-maloyl radical of formula (IVa) or of formula (IVb); and the compound of formula ($Ic_2$) corresponding to formula (I) for which $Q_1$ and $Q_4$ represent the caffeoyl radical of formula (II), $Q_3$ represents the hydroxyl radical and $Q_5$ represents the caffeoyl-maloyl radical of formula (IVa) or of formula (IVb); and c) from 20.0% by mass to 35.0% by mass of water;

wherein said composition (C1) is prepared from a process comprising the following successive stages:

a step a) of cultivating the plant *Arctium lappa* under soilless conditions, fed with a nutrient solution, so as to obtain a biomass ($BM_1$);

a step b) of immersing the roots of said biomass ($BM_1$) obtained in step a) above in a medium(S), such that the roots of said biomass ($BM_1$)/medium ($S_1$) ratio is between 0.5 kg/l and 1.5 kg/l, said medium ($S_1$) comprising, per 100% of its own mass, from 20% to 35% by mass of water, the pH of said water having been adjusted to a value of between 1.5 and 3.5 by addition of a protic acid chosen from sulfuric acid, phosphoric acid and hydrochloric acid, and from 65% to 80% by mass of an organic solvent ($SO_1$) selected from 1,2-propanediol, 1,3-propanediol, 1,4-butanediol, 1,3-butanediol, 1,2-butanediol, 2-methyl-2,4-pentanediol, 1,6-hexanediol, 1,8-octanediol or a mixture of these diols;

a step c) of separating the roots of the biomass at the end of the treatment defined in step b), to isolate a liquid phase ($L_1$) and a biomass ($BM_2$);

a step d) of immersing said biomass ($BM_2$) resulting from step c) in said medium ($S_1$); in a biomass ($BM_2$)/medium ($S_1$) ratio of between 0.1 kg/l and 1.5 kg/l;

a step e) of separating of said biomass ($BM_2$) at the end of the treatment defined in step d), to isolate a liquid phase ($L_2$);

a step f) of filtering said liquid phase ($L_2$) obtained in step e), to remove residual solids and isolate a liquid phase ($L_3$); and a step g) of mixing said liquid phases ($L_1$) and ($L_3$), then, if necessary, adding water and/or said organic solvent ($SO_1$), so as to obtain the expected composition ($C_1$); and II. applying an effective amount of composition $C_1$ to the skin.

2. The method of claim 1, wherein the inflammation is caused by one or more skin pathologies selected from the group consisting of urticaria, rosacea, psoriasis, herpes, photodermatosis, contact dermatitis, lichen, prurigo, pruriginous diseases, fibrosis, disorders of collagen maturation, and scleroderma.

* * * * *